(12) United States Patent
Buesing et al.

(10) Patent No.: US 7,799,875 B2
(45) Date of Patent: Sep. 21, 2010

(54) TRIARYLAMINE-ARYLVINYLENE MOIETY-CONTAINING CONJUGATED POLYMERS, THEIR PRODUCTION AND USE

(75) Inventors: Arne Buesing, Frankfurt Am Main (DE); Aurélie Ludemann, Frankfurt (DE); René Scheurich, Gross-Zimmern (DE)

(73) Assignee: Merck Patent GmbH, Darmstadt (DE)

( * ) Notice: Subject to any disclaimer, the term of this patent is extended or adjusted under 35 U.S.C. 154(b) by 117 days.

(21) Appl. No.: 12/097,782

(22) PCT Filed: Nov. 18, 2006

(86) PCT No.: PCT/EP2006/011085
§ 371 (c)(1), (2), (4) Date: Jun. 17, 2008

(87) PCT Pub. No.: WO2007/068325
PCT Pub. Date: Jun. 21, 2007

(65) Prior Publication Data
US 2009/0005505 A1    Jan. 1, 2009

(30) Foreign Application Priority Data
Dec. 17, 2005 (DE) .................. 10 2005 060 473

(51) Int. Cl.
*C08L 61/00* (2006.01)
*C08G 8/28* (2006.01)

(52) U.S. Cl. .............. 525/509; 252/519.21; 252/582; 428/690; 524/850; 528/4; 528/8

(58) Field of Classification Search ............ 252/519.21, 252/582; 428/690; 524/850; 528/4, 8; 525/509
See application file for complete search history.

(56) References Cited

U.S. PATENT DOCUMENTS

| | | | |
|---|---|---|---|
| 5,621,131 A | 4/1997 | Kreuder et al. | |
| 5,814,244 A | 9/1998 | Kreuder et al. | |
| 6,066,712 A | 5/2000 | Ueda et al. | |
| 6,541,602 B1 | 4/2003 | Spreitzer et al. | |
| 6,653,438 B1 | 11/2003 | Spreitzer et al. | |
| 6,956,095 B2 | 10/2005 | Treacher et al. | |
| 6,994,893 B2 | 2/2006 | Spreitzer et al. | |
| 7,252,781 B2 | 8/2007 | Spreitzer et al. | |
| 7,288,617 B2 | 10/2007 | Treacher et al. | |
| 7,323,533 B2 | 1/2008 | Becker et al. | |
| 2006/0058494 A1 | 3/2006 | Busing et al. | |
| 2006/1014902 | 7/2006 | Parham et al. | |
| 2007/0060736 A1 | 3/2007 | Becker et al. | |
| 2007/0080343 A1 | 4/2007 | Heun et al. | |
| 2007/0154732 A1 | 7/2007 | Kitano et al. | |

FOREIGN PATENT DOCUMENTS

| | | |
|---|---|---|
| DE | 19532574 A1 | 3/1997 |
| EP | 0707020 A2 | 4/1996 |
| EP | 1229063 A2 | 8/2002 |
| EP | 1277824 A1 | 1/2003 |
| EP | 1281745 A1 | 2/2003 |
| EP | 1398340 A1 | 3/2004 |
| WO | WO-97/05184 A1 | 2/1997 |
| WO | WO-97/39045 A1 | 10/1997 |
| WO | WO-99/54385 A1 | 10/1999 |
| WO | WO-00/22026 A1 | 4/2000 |
| WO | WO-00/22027 A1 | 4/2000 |
| WO | WO-00/46321 A1 | 8/2000 |
| WO | WO-02/67343 A1 | 8/2002 |
| WO | WO-02/072714 A1 | 9/2002 |
| WO | WO-02/077060 A1 | 10/2002 |
| WO | WO-03/019694 A2 | 3/2003 |
| WO | WO-03/020790 A2 | 3/2003 |
| WO | WO-03/048225 A2 | 6/2003 |
| WO | WO-2004/037887 A2 | 5/2004 |
| WO | WO-2004/070772 A2 | 8/2004 |
| WO | WO-2005/014689 A2 | 2/2005 |
| WO | WO-2005/026144 A1 | 3/2005 |
| WO | WO-2005/030828 A1 | 4/2005 |
| WO | WO-2005/040302 A1 | 5/2005 |

*Primary Examiner*—Terressa M Boykin
(74) *Attorney, Agent, or Firm*—Connolly Bove Lodge & Hutz LLP

(57) ABSTRACT

The present invention relates to conjugated polymers and dendrimers containing styryl-triarylamine structural units, to the use thereof in electronic components, in particular in polymeric organic light-emitting diodes, to monomers for the preparation thereof, and to components and light-emitting diodes comprising polymers and dendrimers of this type.

23 Claims, No Drawings

TRIARYLAMINE-ARYLVINYLENE MOIETY-CONTAINING CONJUGATED POLYMERS, THEIR PRODUCTION AND USE

RELATED APPLICATIONS

This application is a national stage application (under 35 U.S.C. §371) of PCT/EP2006/011085, filed Nov. 18, 2006, which claims benefit of German application 10 2005 060 473.0, filed Dec. 17, 2005.

The present invention relates to conjugated polymers and dendrimers containing styryl-triarylamine structural units, to the use thereof in electronic components, in particular in polymeric organic light-emitting diodes, to monomers for the preparation thereof, and to components and light-emitting diodes comprising polymers and dendrimers of this type.

Conjugated polymers are currently being intensively investigated as highly promising materials in PLEDs (polymeric light emitting diodes). Their simple processing in contrast to SMOLEDs (small molecule organic light emitting diodes) promises less expensive production of corresponding light-emitting diodes.

For the generation of all three emission colours, it is necessary here to copolymerise certain comonomers into the corresponding polymers (cf., for example, WO 00/46321, WO 03/020790 and WO 02/077060). Thus, it is then generally possible—starting from a blue-emitting base polymer ("backbone")—to generate the two other primary colours red and green.

Some of the conjugated polymers in accordance with the prior art already exhibit good properties on use in PLEDs. In spite of the advances achieved in recent years, however, these polymers still do not meet the requirements made of them for high-quality applications. Thus, the photostability of the polymers in accordance with the prior art is still in no way satisfactory, i.e. the polymers in some cases decompose on exposure to light. This applies, in particular, in the case of irradiation with blue and UV light. As a consequence, the efficiency of the light emission by the polymers drops drastically. It would thus be desirable to have available here polymers which do not exhibit these problems, but whose other properties in the device are just as good or better than the device properties of the polymers in accordance with the prior art.

In accordance with the prior art, conjugated polymers based on fluorenes, indenofluorenes, spirobifluorenes, phenanthrenes and dihydrophenanthrenes, in particular, are synthesised today in order to be able to produce blue-luminescent organic light-emitting diodes. Two-layer structures, in which an emission layer is applied to an injection layer, are increasingly finding acceptance here.

However, the systems described above have deficiencies in the following parameters:

The lifetime of the blue-emitting polymers is by far not yet sufficient for use in mass products.

The efficiency of the polymers prepared in accordance with the prior art is too low.

The operating voltages are too high for the potential applications.

The materials frequently suffer from a shift in the emission characteristics during operation.

Surprisingly, it has now been found that conjugated polymers containing triarylamine units which are substituted by a styryl group are very good as blue- or green-emitting unit and have properties which are superior to the prior art. This relates, inter alia, to the photostability, but also to the efficiency of the polymers. In particular, it has been found that the incorporation of triphenylamines which are substituted by a styryl group into the emission layer of a polymer in low concentrations results in an increase in the lifetime and efficiency and a reduction in the operating voltage with a slight shift in the emission colour. The present invention therefore relates to these polymers and to the use thereof in PLEDs.

Polymers for OLEDs containing vinyl and triarylamine groups are disclosed in EP 1 281 745 A1, EP 1 277 824 A1 and U.S. Pat. No. 6,066,712. However, polymers in accordance with the present invention are not indicated therein.

The invention relates to conjugated polymers and dendrimers, characterised in that they contain one or more units of the formula (1)

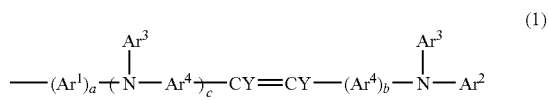

(1)

where the symbols and indices used have the following meaning:

$Ar^1$ is on each occurrence, identically or differently, mono- or polycyclic aryl or heteroaryl, which may be mono- or polysubstituted by $R^1$, $Ar^1$ is on each occurrence, identically or differently, mono- or polycyclic aryl or heteroaryl, which may be mono- or polysubstituted by $R^2$ $Ar^3$ is on each occurrence, identically or differently, mono- or polycyclic aryl or heteroaryl, which may be mono- or polysubstituted by $R^3$, $Ar^4$ is on each occurrence, identically or differently, mono- or polycyclic aryl or heteroaryl, which may be mono- or polysubstituted by $R^4$, Y is on each occurrence, identically or differently, H, F, Cl or a carbon or hydrocarbon radical having 1 to 40 C atoms, in which, in addition, two radicals Y, or one radical Y and an adjacent radical $R^1$, $R^4$, $Ar^1$ or $Ar^4$, may form an aliphatic or aromatic, mono- or polycyclic ring system with one another, $R^{1-4}$ are on each occurrence, identically or differently, H, F, Cl, OH, CN, $N(R)_2$, $Si(R)_3$, $B(R)_2$ or a carbon or hydrocarbon radical having 1 to 40 C atoms, in which, in addition, two or more of the radicals $R^{1-4}$ may form an aliphatic or aromatic, mono- or polycyclic ring system with one another, $R^1$, $R^2$ and $R^3$ may also denote a covalent link in the polymer or dendrimer, R is on each occurrence, identically or differently, H or a straight-chain, branched or cyclic alkyl having 1 to 22 C atoms, in which, in addition, one or more non-adjacent $CH_2$ groups may be replaced by —C($R^0$)=C($R^0$)—, —C≡C—, —N($R^0$)—, —Si($R^0$)$_2$—, —O—, —S—, —CO—, —CO—O—, —O—CO—, —O—CO—O—, —S—CO—, —CO—S— in such a way that O and/or S atoms are not linked directly to one another and in which one or more H atoms may be replaced by F, Cl or CN, or aryl having 5 to 40 C atoms, in which, in addition, one or more C atoms may be replaced by O, S or N, where these groups may also be substituted by one or more non-aromatic radicals $R^1$; a plurality of radicals R, or radicals R with further radicals $R^{1-4}$, may also form an aromatic or aliphatic, mono- or polycyclic ring system here, $R^0$ is on each occurrence, identically or differently, H or an aliphatic or aromatic hydrocarbon radical having 1 to 20 C atoms, a is on each occurrence, identically or differently, 1, 2 or 3,
b is on each occurrence, identically or differently, 1, 2 or 3,
c is on each occurrence, identically or differently, 0 or 1.

The linking of the units of the formula (1) to adjacent units in the polymers according to the invention can take place along the polymer main chain or also in the polymer side chain.

Particular preference is given to polymers containing one or more units of the formula (1), preferably in the polymer main chain, in which $A^2$ has a substituent $R^2$ which denotes a link.

Preference is furthermore given to polymers containing one or more units of the formula (1), preferably in the polymer side chain, in which $Ar^2$ and $Ar^3$ have no substituents $R^2$ or $R^3$ which denote a link.

Preference is furthermore given to branched polymers containing one or more units of the formula (1) in which $Ar^2$ and one or more radicals $Ar^3$ each have a substituent $R^2$ or $R^3$ which denotes a link, i.e. polymers containing at least one unit of the formula (1) as a branching point.

Preference is furthermore given to dendrimers containing one or more units of the formula (1) in which Ar and one or more radicals $Ar^3$ each have a substituent $R^2$ or $R^3$ which denotes a link.

Although this is evident from the description, it should again explicitly be pointed out here that the structural units of the formula (1) may be asymmetrically substituted, i.e. different substituents $R^{1-4}$ may be present on one unit.

Above and below, the term "carbon radical" denotes a mono- or polyvalent organic radical containing at least one carbon atom which either contains no further atoms (such as, for example, —C≡C—), or optionally contains one or more further atoms, such as, for example, N, O, S, P, Si, Se, As, Te or Ge (for example carbonyl, etc.). The term "hydrocarbon radical" denotes a carbon radical which additionally contains one or more H atoms and optionally one or more heteroatoms, such as, for example, N, O, S, P, Si, Se, As, Te or Ge.

The term "aryl" denotes an aromatic carbon group or a group derived therefrom. The term "heteroaryl" denotes "aryl" in accordance with the above definition containing one or more heteroatoms.

The carbon or hydrocarbon radical may be a saturated or unsaturated group. Unsaturated groups are, for example, aryl, alkenyl or alkynyl groups. A carbon or hydrocarbon radical having more than 3 C atoms may be straight-chain, branched and/or cyclic and may also have spiro links or condensed rings.

Further preferred carbon and hydrocarbon radicals are straight-chain, branched or cyclic alkyl having 1 to 40, preferably 1 to 22, C atoms, which is unsubstituted or mono- or polysubstituted by F, Cl, Br, I or CN and in which one or more non-adjacent $CH_2$ groups may each be replaced, independently of one another, by —C($R^0$)=C($R^0$)—, —C≡C—, —N($R^0$)—, —O—, —S—, —CO—, —CO—O—, —O—CO—, —S—CO—, —CO—S—, —O—CO—O— in such a way that O and/or S atoms are not linked directly to one another, or aryl having 5 to 40 C atoms, which is optionally mono- or polysubstituted by R and in which one or more C atoms may be replaced by O, S or N, where R and $R^0$ have the meanings indicated above.

Particularly preferred carbon and hydrocarbon radicals are straight-chain, branched or cyclic alkenyl, alkynyl, alkoxy, alkylcarbonyl, alkoxycarbonyl, alkylcarbonyloxy and alkoxycarbonyloxy having 1 to 40, preferably 1 to 25, particularly preferably 1 to 18, C atoms, optionally substituted aryl or aryloxy having 5 to 40, preferably 5 to 25, C atoms, or optionally substituted alkylaryl, arylalkyl, alkylaryloxy, arylalkyloxy, arylcarbonyl, aryloxycarbonyl, arylcarbonyloxy and aryloxycarbonyloxy having 5 to 40, preferably 5 to 25, C atoms.

Very particularly preferred carbon and hydrocarbon radicals are $C_1$-$C_{40}$ alkyl, $C_2$-$C_{40}$ alkenyl, $C_2$-$C_{40}$ alkynyl, $C_3$-$C_{40}$ alkyl, $C_4$-$C_{40}$ alkyldienyl, $C_4$-$C_{40}$ polyenyl, $C_6$-$C_{40}$ aryl, $C_6$-$C_{40}$ alkylaryl, $C_6$-$C_{40}$ arylalkyl, $C_6$-$C_{40}$ alkylaryloxy, $C_6$-$C_{40}$ arylalkyloxy, $C_6$-$C_{40}$ heteroaryl, $C_4$-$C_{40}$ cycloalkyl, $C_4$-$C_{40}$ cycloalkenyl, etc. Particular preference is given to $C_1$-$C_{22}$ alkyl, $C_2$-$C_{22}$ alkenyl, $C_2$-$C_{22}$ alkynyl, $C_3$-$C_{22}$ alkyl, $C_4$-$C_{22}$ alkyldienyl, $C_6$-$C_{12}$ aryl, $C_6$-$C_{20}$ arylalkyl and $C_6$-$C_{20}$ heteroaryl.

Preferred alkyl groups are, for example, methyl, ethyl, n-propyl, isopropyl, n-butyl, isobutyl, s-butyl, t-butyl, 2-methylbutyl, n-pentyl, s-pentyl, cyclopentyl, n-hexyl, cyclohexyl, 2-ethylhexyl, n-heptyl, cycloheptyl, 1,175-trimethylheptyl, n-octyl, cyclooctyl, dodecanyl, trifluoromethyl, perfluoro-n-butyl, 2,2,2-trifluoroethyl, perfluorooctyl, perfluorohexyl, etc.

Preferred alkenyl groups are, for example, ethenyl, propenyl, butenyl, pentenyl, cyclopentenyl, hexenyl, cyclohexenyl, heptenyl, cycloheptenyl, octenyl, cyclooctenyl, etc.

Preferred alkynyl groups are, for example, ethynyl, propynyl, butynyl, pentynyl, hexynyl, octynyl, etc.

Preferred alkoxy groups are, for example, methoxy, ethoxy, 2-methoxyethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, n-decoxy, etc.

Preferred amino groups are, for example, dimethylamino, methylamino, methylphenylamino, phenylamino, etc.

Aryl groups may be monocyclic or polycyclic, i.e. they may have one ring (for example phenyl) or two or more rings, which may also be condensed (for example naphthyl) or covalently linked (for example biphenyl), or contain a combination of condensed and linked rings. Preference is given to fully conjugated aryl groups.

Preferred aryl groups are, for example, phenyl, biphenyl, triphenyl, 1,1',3',1''-terphenyl-2'-yl, naphthyl, anthracene, binaphthyl, phenanthrene, pyrene, dihydropyrene, chrysene, perylene, tetracene, pentacene, benzopyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]-thiophene, thieno[3,2b]thiophene, dithienothiophene, isobenzothiophene, dibenzothiophene, benzothiadiazothiophene, or combinations of these groups. The heteroaryl groups may also be substituted by alkyl, alkoxy, thioalkyl, fluorine, fluoroalkyl or other aryl or heteroaryl groups.

The aryl, heteroaryl, carbon and hydrocarbon radicals optionally have one or more substituents, which are preferably selected from the group consisting of silyl, sulfo, sulfonyl, formyl, amine, imine, nitrile, mercapto, nitro, halogen, $C_{1-12}$ alkyl, $C_{6-12}$ aryl, $C_{1-12}$ alkoxy, hydroxyl, or combinations of these groups.

Preferred substituents are, for example, solubility-promoting groups, such as alkyl or alkoxy, electron-withdrawing groups, such as fluorine, nitro or nitrile, or substituents for increasing the glass-transition temperature (Tg) in the polymer, in particular bulky groups, such as, for example, t-butyl or optionally substituted aryl groups.

Further preferred substituents are, for example, F, Cl, Br, I, —CN, —NO$_2$, —NCO, —NCS, —OCN, —SCN, —C(=O)N(R$^0$)$_2$, —C(=O)X, —C(=O)R$^0$, —N(R$^0$)$_2$, in which X denotes halogen and R$^0$ has the meaning indicated above, optionally substituted silyl, aryl having 4 to 40, preferably 6 to 20, C atoms, and straight-chain or branched alkyl, alkoxy, alkylcarbonyl, alkoxycarbonyl, alkylcarbonyloxy or alkoxycarbonyloxy having 1 to 22 C atoms, in which one or more H atoms may optionally be replaced by F or Cl.

The terms "alkyl", "aryl", "heteroaryl", etc., also encompass polyvalent groups, for example alkylene, arylene, heteroarylene, etc.

"Halogen" denotes F, Cl, Br or I.

For the purposes of this invention, "conjugated polymers" are polymers which contain principally sp$^2$-hybridised (or optionally also sp-hybridised) carbon atoms, which may also be replaced by corresponding heteroatoms, in the main chain. In the simplest case, this means the alternating presence of double and single bonds in the main chain, but also polymers containing units such as, for example, meta-linked phenylene are intended to be regarded as conjugated polymers for the purposes of this invention. "Principally" means that naturally (randomly) occurring defects which result in conjugation interruptions do not devalue the term "conjugated polymer". Furthermore, the term "conjugated" is likewise used in this application text if the main chain contains, for example, arylamine units, arylphosphine units and/or certain heterocycles (i.e. conjugation via N, O, P or S atoms) and/or organometallic complexes (i.e. conjugation via the metal atom). An analogous situation applies to conjugated dendrimers.

The term "dendrimer" here is intended to be taken to mean a highly branched compound which is built up from a multifunctional centre (core) to which branched monomers are bonded in a regular construction, giving a tree-like structure. Both the core and also the monomers here can adopt any desired branched structures which consist both of purely organic units and also organometallic compounds or coordination compounds. "Dendrimer" here is in general intended to be understood as described, for example, by M. Fischer and F. Vögtie (*Angew. Chem., Int. Ed.* 1999, 38, 885).

The units of the formula (1) can be incorporated in accordance with the invention into the main or side chain of the polymer. In the case of incorporation into the side chain, it is possible for the unit of the formula (1) to be in conjugation with the polymer main chain or to be non-conjugated with the polymer main chain.

In a preferred embodiment of the invention, the unit of the formula (1) is in conjugation with the polymer main chain. This can be achieved on the one hand by incorporating this unit into the main chain of the polymer in such a way that the conjugation of the polymer, as described above, is thereby retained. On the other hand, this unit can also be linked into the side chain of the polymer in such a way that conjugation with the main chain of the polymer exists. This is the case, for example, if the linking to the main chain takes place only via sp$^2$-hybridised (or optionally also via sp-hybridised) carbon atoms, which may also be replaced by corresponding heteroatoms. However, if the linking takes place through units such as, for example, simple (thio)ether bridges, esters, amides or alkylene chains, the structural unit of the formula (1) is defined as non-conjugated with the main chain.

The linking of the units of the formula (1) to the main chain can take place directly or via one or more additional units. Preferred units for the linking are optionally substituted, straight-chain, branched or cyclic alkylene groups, alkenylene groups or alkynylene groups, in particular optionally substituted C=C double bonds, C≡C triple bonds, or aromatic units, further di- and triarylamino units, aryleneviнylene units or aryleneethynylene units which are identical to or different from formula (1). Preference is given to linking in conjugation with the main chain.

The radicals R$^{1-4}$ in formula (1) are preferably selected from the above-mentioned groups.

The radicals Ar$^{1-3}$ in formula (1) preferably denote phenyl (as monovalent radical) or phenylene (as divalent radical), where these groups may be mono- or polysubstituted by R$^5$, and R$^5$ has one of the meanings indicated for R$^4$ in formula (1). If one of the phenylene radicals Ar$^{1-3}$ has a link to an adjacent unit, this is located in the 2-, 3- or 4-position, preferably in the 4-position.

The radicals Ar$^4$ in formula (1) are preferably selected from phenylene, in particular 1,4-phenylene, 4,4'-biphenylene, 9,9-disubstituted fluorene-2,7-diyl, or 6,6,12,12-tetra substituted indenofluorene-2,8-diyl or spirobifluorene-2,7-diyl, where these groups may be mono- or polysubstituted by R$^5$ as defined above.

The groups Y in formula (1) preferably denote H or form an unsaturated, 5- or 6-membered, optionally substituted ring system with the adjacent group Ar$^4$.

Particular preference is given to polymers and dendrimers according to the invention containing one or more units of the formula (1) selected from the following sub-formulae:

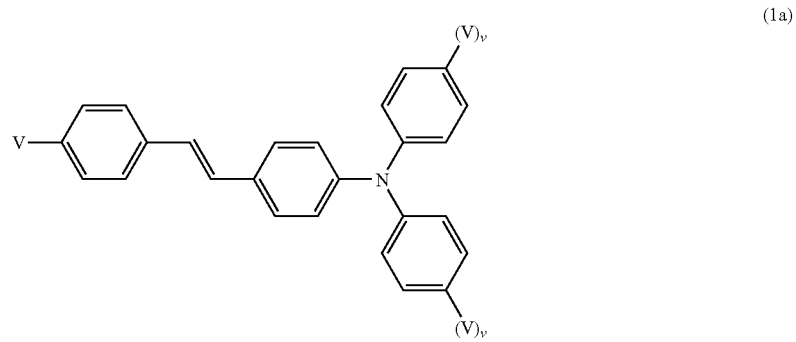

(1a)

-continued
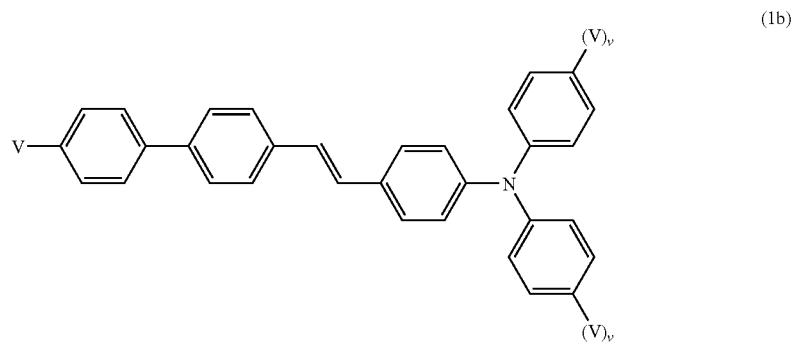
(1b)
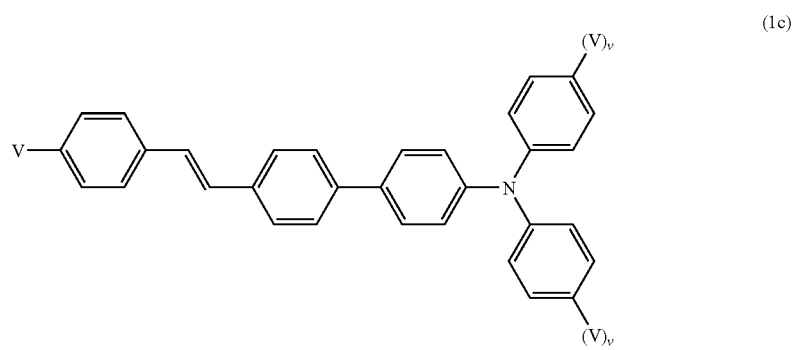
(1c)
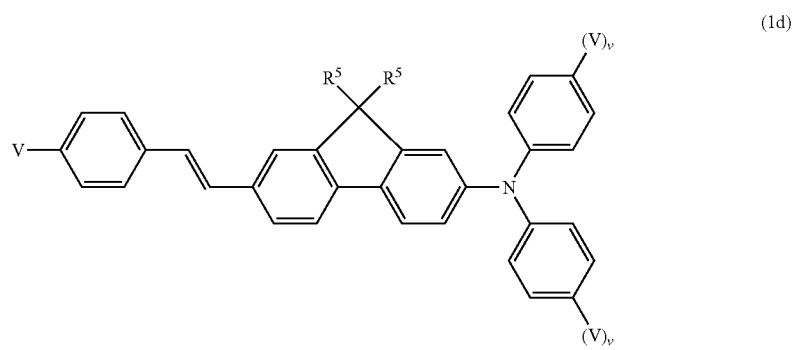
(1d)
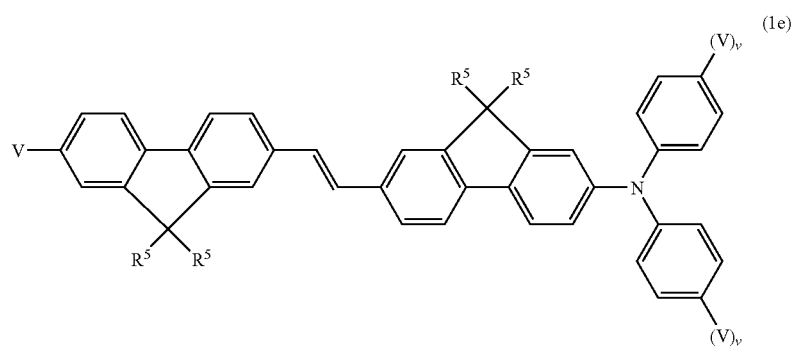
(1e)

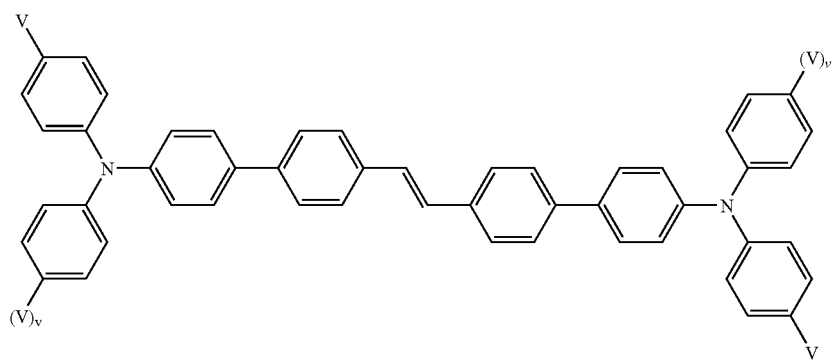
(1f)
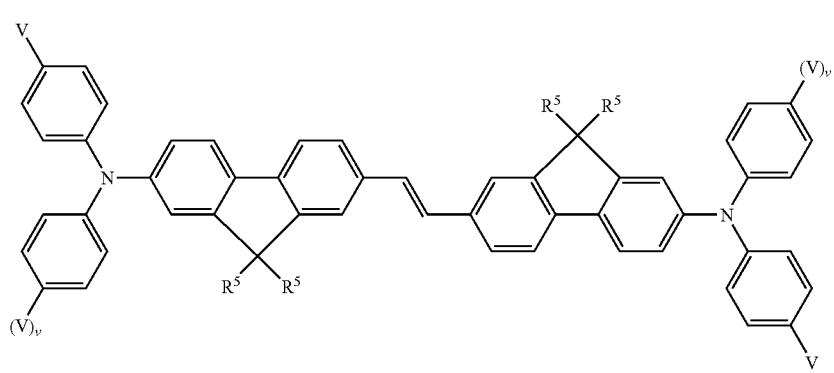
(1g)
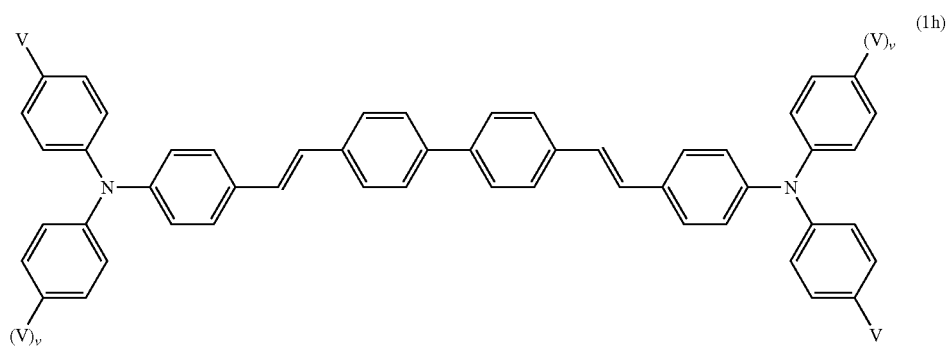
(1h)
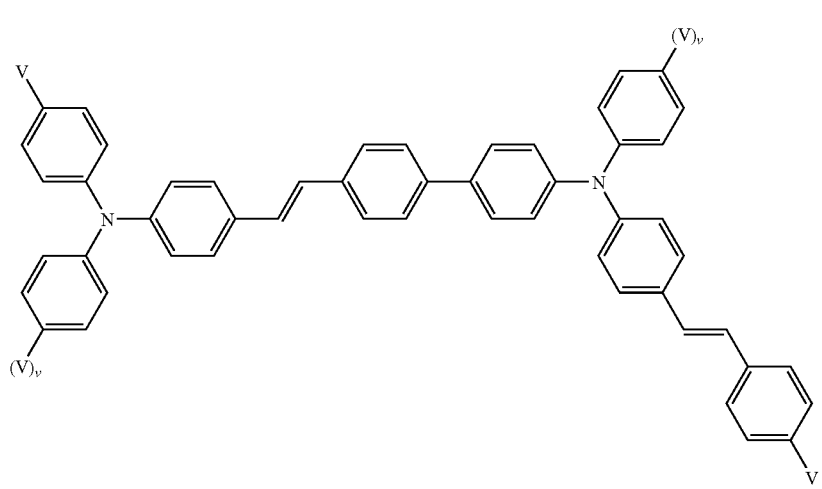
(1i)

-continued

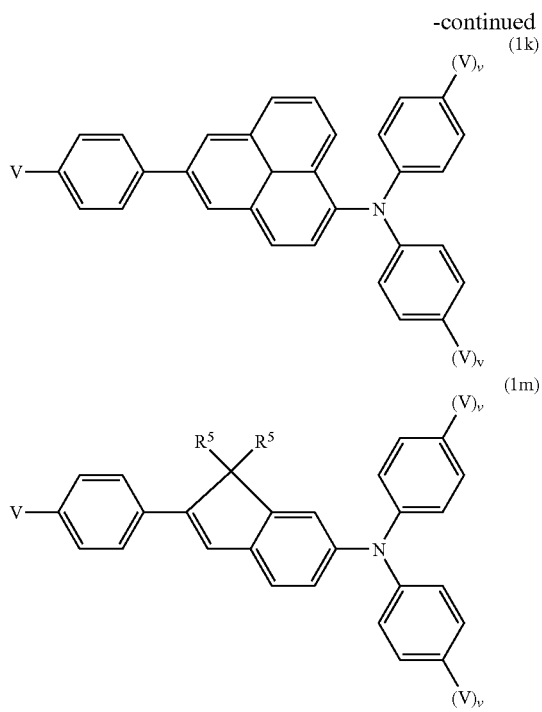

(1k)

(1m)

in which V denotes a covalent link in the polymer or dendrimer, and v denotes 0 or 1, and $R^5$ on each occurrence, identically or differently, has one of the meanings indicated for $R^4$ in formula (1). The phenyl rings may also be mono- or polysubstituted by $R^5$.

The conjugated polymers and dendrimers according to the invention preferably contain at least 0.5 mol %, in particular 1 to 50 mol %, particularly preferably 1 to 30 mol %, very particularly preferably 1 to 10 mol %, of one or more units of the formula (1).

The structural unit of the formula (1) is accessible readily and in high yields. Compounds containing this structural unit, such as, for example, the following compound

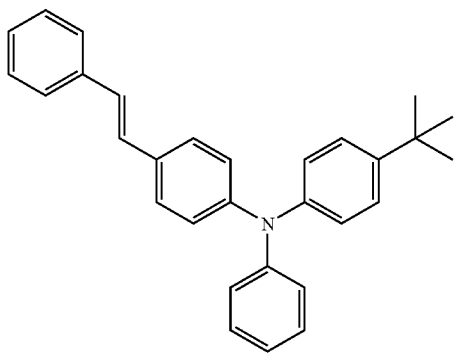

exhibit intense green-blue luminescence in the solid. In low concentration in solution, by contrast, dark-blue luminescence is obtained. Any adjustment of the emission colour that may be necessary can be carried out through the choice of the substituents on the phenyl ring which is not incorporated into the polymer chain.

The compounds of the formula I can be prepared by methods known to the person skilled in the art and described in the literature. Further suitable and preferred synthetic processes are given in the examples. The compounds of the formula I can be prepared, for example, by reacting optionally substituted phenyl-4-bromophenyl-4-formylphenylamine, which can be prepared by processes known from the literature, with optionally substituted diethyl 4-bromobenzylphosphonate in the presence of a base.

The invention furthermore relates to the processes described above and below.

Particular preference is given to polymers according to the invention which also contain further structural elements in addition to units of the formula (I) and should thus be regarded as copolymers. Although the further comonomers are necessary for the synthesis of the copolymers according to the invention, they are, however, not themselves a subject-matter of the present invention and should thus be described by reference. Reference should also be made here, in particular, to the relatively extensive lists in WO 02/077060, WO 2005/014689 and the references cited therein.

These further structural units can originate, for example, from the classes described below:

Group 1: Comonomers which represent the polymer backbone.

Group 2: Comonomers which increase the hole-injection and/ or -transport properties of the polymers.

Group 3: Comonomers which significantly increase the electroninjection and/or -transport properties of the polymers.

Group 4: Comonomers which have combinations of individual units from group 2 and group 3.

Suitable and preferred units for the above-mentioned groups are described below.

Group 1—comonomers which represent the polymer backbone:

Preferred units from group 1 are, in particular, those which contain aromatic or carbocyclic structures having 6 to 40 C atoms. Suitable and pre-ferred units are, inter alia, fluorene derivatives, as disclosed, for example, in EP 0842208, WO 99/54385, WO 00/22027, WO 00/22026 or WO 00/46321, furthermore spirobifluorene derivatives, as disclosed, for example, in EP 0707020, EP 0894107 and WO 03/020790, or dihydrophenanthrene derivatives, as disclosed in WO 2005/014689. It is also possible to use a combination of two or more of these monomer units, as described, for example, in WO 02/077060. Other structural elements which are able to influence the morphology, but also the emission colour of the resultant polymers are also possible. Preference is given here to substituted or unsubstituted aromatic structures which have 6 to 40 C atoms, or also stilbene or bisstyrylarylene derivatives, such as, for example, 1,4-phenylene, 1,4-naphthylene, 1,4- or 9,10-anthrylene, 1,6- or 2,7- or 4,9-pyrenylene, tetrahydropyrenylene, 3,9- or 3,10-perylenylene, 2,7- or 3,6-phenanthrenylene, 4,4'-biphenylylene, 4,4"-terphenylylene, 4,4'-bi-1,1'-naphthylylene, 4,4'-stilbenzyl or 4,4"-bisstyrylarylene derivatives.

Preferred units for the polymer backbone are spirobifluorenes, indenofluorenes, phenanthrenes and dihydrophenanthrenes.

Particularly preferred units from group 1 are divalent units of the following formulae, in which the dashed line denotes the link to the adjacent unit:

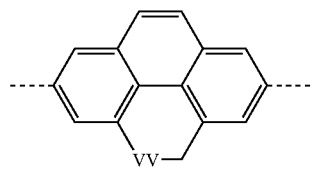

(I)

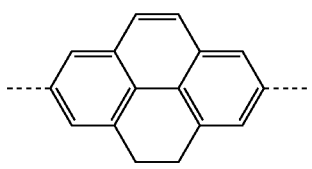

(II)

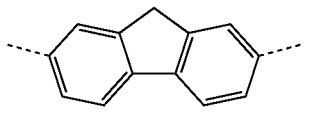

(III)

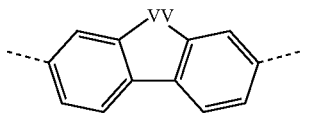

(IV)

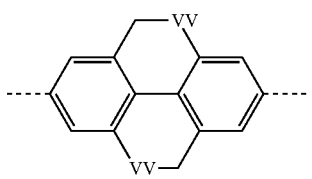

(V)

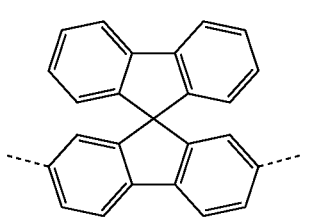

(VI)

-continued

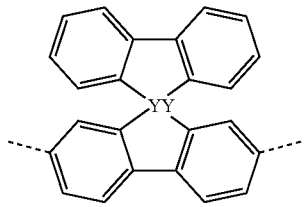

(VII)

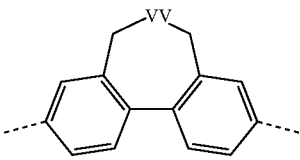

(VIII)

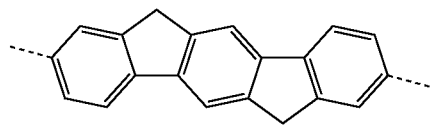

(IX)

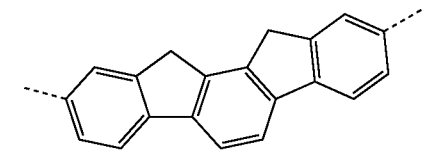

(X)

where the various positions may also be substituted by one or more substituents $R^5$ as defined above, YY denotes Si or Ge, and VV denotes O, S or Se.

Group 2—comonomers which increase the hole-injection and/or -transport properties of the polymers:

These are generally aromatic amines or electron-rich heterocycles, such as, for example, substituted or unsubstituted triarylamines, benzidines, tetraarylene-para-phenylenediamines, phenothiazines, phenoxazines, dihydrophenazines, thianthrenes, dibenzo-p-dioxins, phenoxathiynes, carbazoles, azulenes, thiophenes, pyrroles, furans and further O-, S- or N-containing heterocycles having a high HOMO (HOMO highest occupied molecular orbital). However, triarylphosphines, as described in the unpublished application EP 03018832.0, are also suitable here.

Particularly preferred units from group 2 are divalent units of the following formulae, in which the dashed fine denotes the link to the adjacent unit:

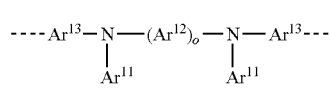

(XI)

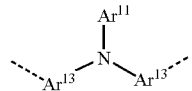

(XII)

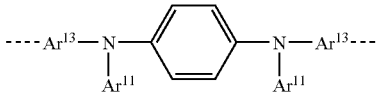

(XIII)

-continued

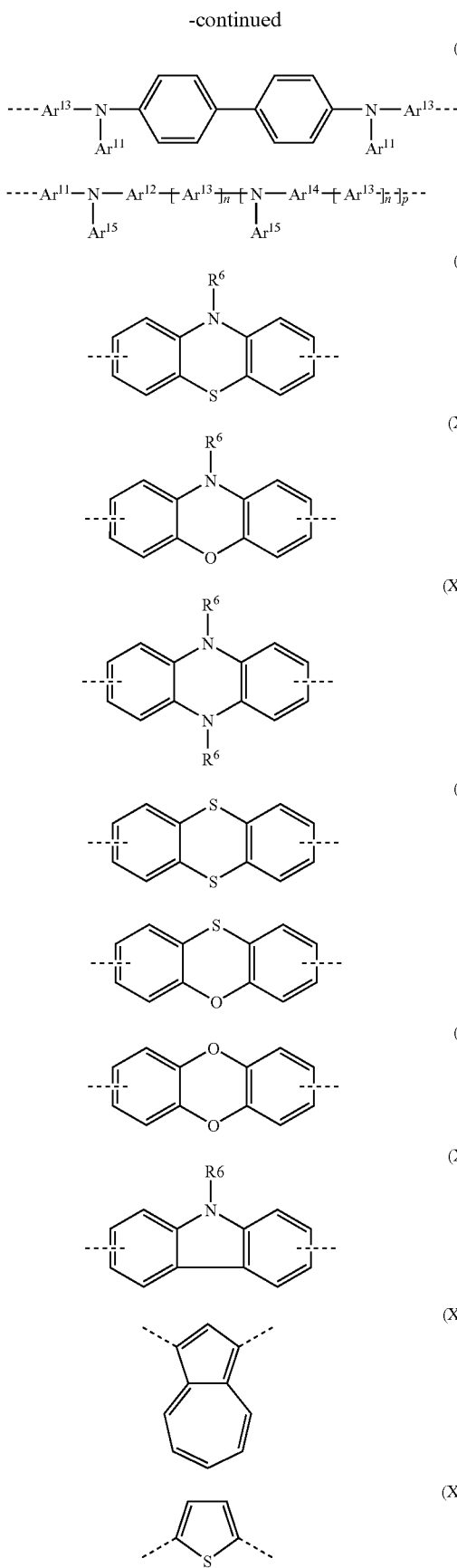

(XIV)
(XV)
(XVI)
(XVII)
(XVIII)
(XIX)
(XX)
(XXI)
(XXII)
(XXIII)
(XXIV)

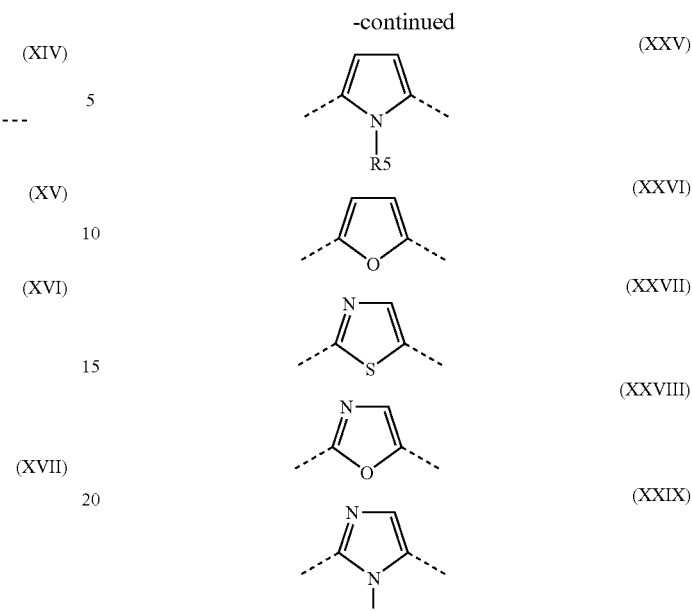

(XXV)
(XXVI)
(XXVII)
(XXVIII)
(XXIX)

where $R^6$ has one of the meanings indicated for $R^5$, the various formulae may also additionally be substituted in the free positions by one or more substituents $R^5$, and the symbols and indices have the following meaning:

n is, identically or differently on each occurrence, 0, 1 or 2, p is, identically or differently on each occurrence, 0, 1 or 2, preferably 0 or 1, o is, identically or differently on each occurrence, 1, 2 or 3, preferably 1 or 2, $Ar^{11}$, $Ar^{13}$ are on each occurrence, identically or differently, an aromatic or heteroaromatic ring system having 2 to 40 C atoms, which may be mono- or polysubstituted by $R^5$ or also unsubstituted; the possible substituents $R^5$ here may potentially be in any free position, $Ar^{12}$, $Ar^{14}$ are on each occurrence, identically or differently, $Ar^{11}$, $Ar^{13}$ or a substituted or unsubstituted stilbenzylene or tolanylene unit, $Ar^{15}$ is, identically or differently on each occurrence, either a system as described by $Ar^{11}$ or an aromatic or heteroaromatic ring system having 9 to 40 aromatic atoms (C or heteroatoms), which may be mono- or polysubstituted by $R^5$ or unsubstituted and which consists of at least two condensed rings; the possible substituents $R^5$ here may potentially be in any free position.

Group 3—comonomers which significantly increase the electron-injection and/or -transport properties of the polymers:

These are generally electron-deficient aromatics or heterocycles, such as, for example, substituted or unsubstituted pyridines, pyrimidines, pyridazines, pyrazines, anthracenes, oxadiazoles, quinolines, quinoxalines or phenazines, but also compounds such as triarylboranes and further O-, S- or N-containing heterocycles having a low LUMO (LUMO=lowest unoccupied molecular orbital), and benzophenones and derivatives thereof, as disclosed, for example, in WO 05/040302.

Particularly preferred units from group 3 are divalent units of the following formulae, in which the dashed line denotes the link to the adjacent unit:

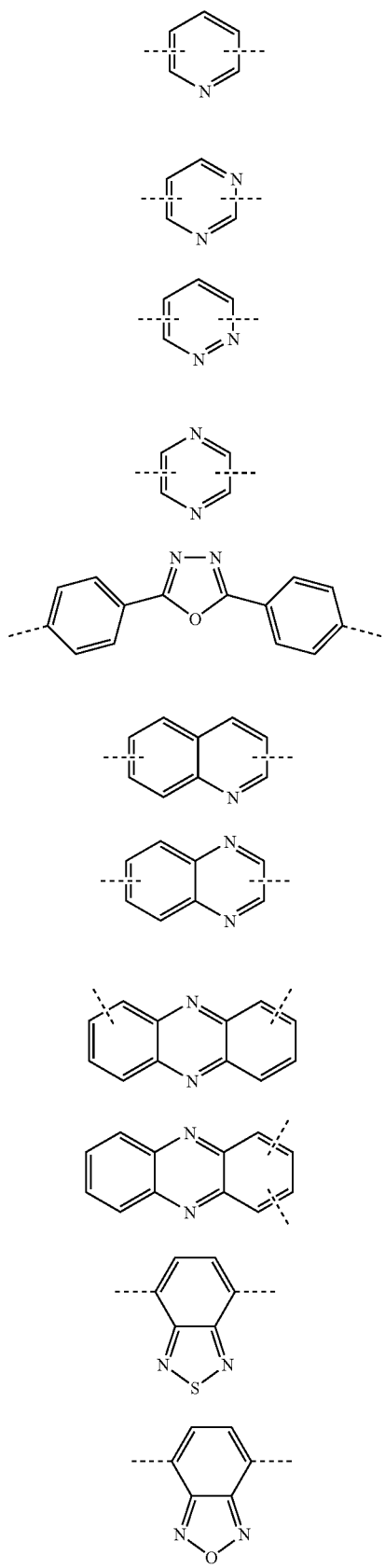

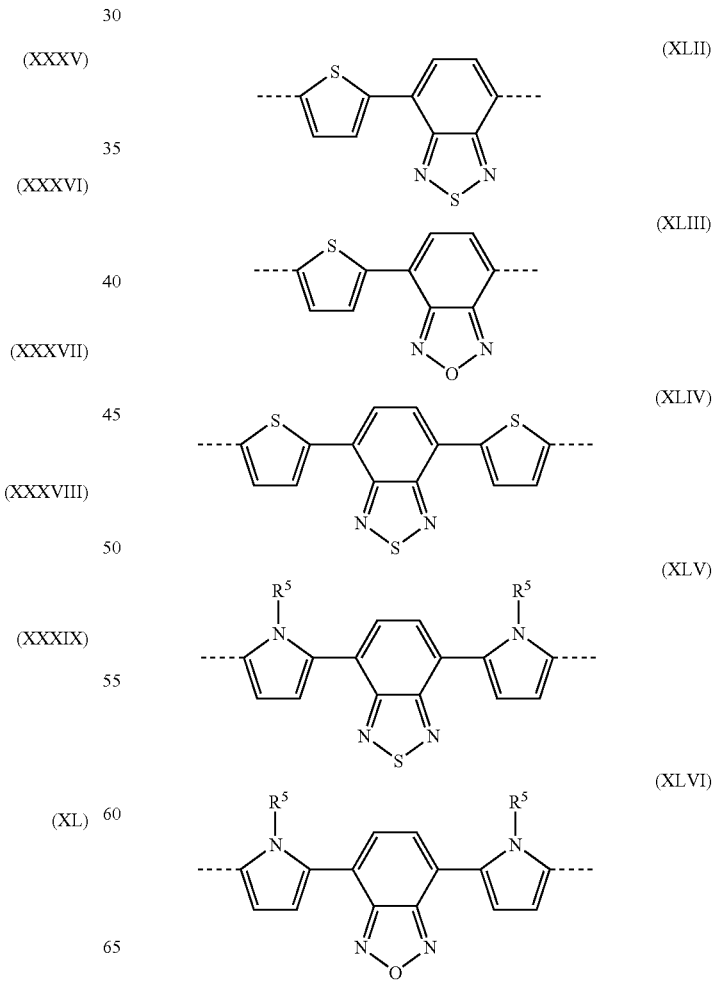

where the various formulae may be substituted in the free positions by one or more substituents $R^5$ as defined above.

Group 4—comonomers which have combinations of individual units from group 2 and group 3:

It is also possible for the polymers according to the invention to contain units in which structures which increase the hole mobility and the electron mobility are bonded directly to one another. However, some of these units shift the emission colour into the yellow or red; their use in polymers according to the invention for the generation of blue or green emission is therefore less preferred.

If such units from group 4 are present in the polymers according to the invention, they are preferably selected from divalent units of the following formulae, in which the dashed line denotes the link to the adjacent unit:

where the various formulae may be substituted in the free positions by one or more substituents $R^5$ as defined above, the symbols $R^5$, $R^6$, $Ar^{11}$, n, p and o have the above-mentioned meaning, and $Y^1$ is on each occurrence, identically or differently, O, S, Se, N, P, Si or Ge.

It is also possible for more than one structural unit from one of groups 1-4 to be present simultaneously.

The polymer according to the invention may furthermore likewise contain metal complexes, which are generally built up from one or more ligands and one or more metal centres, bonded into the main or side chain.

Preference is given to polymers according to the invention which at the same time, besides structural units of the formula (1), additionally also contain one or more units selected from groups 1 to 4.

Preference is given here to polymers according to the invention which, besides units of the formula (1), also contain units from group 1, particularly preferably at least 50 mol % of these units.

It is likewise preferred for the polymers according to the invention to contain units which improve the charge transport or charge injection, i.e. units from group 2 and/or 3; a proportion of 1-30 mol % of these units is particularly preferred; a proportion of 1-10 mol % of these units is very particularly preferred.

It is furthermore particularly preferred for the polymers according to the invention to contain units from group 1 and units from group 2 and/or 3, in particular at least 50 mol % of units from group 1 and 1-30 mol % of units from group 2 and/or 3.

The polymers according to the invention generally have 10 to 10,000, preferably 20 to 5000, particularly preferably 50 to 2000, recurring units. Corresponding dendrimers may also have fewer recurring units.

The requisite solubility of the polymers and dendrimers is ensured, in particular, by the substituents on the various recurring units, both by substituents R and $R^{1-4}$ on units of the formula (1) and also by substituents on the other recurring units.

The polymers according to the invention are either homopolymers comprising units of the formula (1) or copolymers. The polymers according to the invention may be linear or branched (crosslinked). Besides one or more structures of the formula (1), or preferred sub-formulae thereof, copolymers according to the invention may potentially have one or more further structures from groups 1 to 4 mentioned above.

The copolymers according to the invention may have random, alternating or block-like structures or also have a plurality of these structures in an alternating arrangement. The way in which copolymers having block-like structures can be obtained and which further structural elements are particularly preferred for this purpose is described in detail, for example, in WO 2005/014688. This is incorporated into the present application by way of reference. It should likewise be re-emphasised at this point that the polymer may also have dendritic structures.

It may also be preferred for a significantly smaller proportion than 1 mol % of structural units of the formula (1) to be used. Thus, 0.01 to 1 mol % of such units, for example as blue- or green-emitting units, can be used for the synthesis of white-emitting copolymers. For this purpose, only a small proportion of blue- or green-emitting units is generally required, as described in WO 2005/030828. The invention thus also relates to the use of structural units of the formula (1) for the synthesis of white-emitting copolymers.

Structural units of the formula (1) can likewise be used as green- or blue-emitting comonomers for the synthesis of red-emitting polymers. The invention thus furthermore relates to the use of structural units of the formula (1) for the synthesis of red-emitting polymers.

The polymers according to the invention are generally prepared by polymerisation of one or more types of monomer, at least one monomer of which is described by the formula (1). Suitable polymerisation reactions are known to the person skilled in the art and are described in the literature. Particularly suitable and preferred polymerisation reactions, all of which result in C—C links, are the following:

(A) SUZUKI polymerisation;

(B) YAMAMOTO polymerisation;

(C) STILLE polymerisation.

The way in which the polymerisation can be carried out by these methods and the way in which the polymers can then be separated off from the reaction medium and purified are known to the person skilled in the art and are described in detail in the literature, for example in WO 2004/037887.

The C—C linking reactions are preferably selected from the groups of the SUZUKI coupling, the YAMAMOTO coupling and the STILLE coupling.

The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterisation of dendritic molecules", Materials Science and Technology (1999), 20 (Synthesis of Polymers), 403-458; Tomalia, Donald A., "Dendrimer molecules", Scientific American (1995), 272(5), 62-6, WO 02/67343 A1 or WO 2005/026144 A1.

For the synthesis of the polymers and dendrimers, the corresponding monomers are required. The synthesis of units from groups 1 to 4 is known to the person skilled in the art and is described in the literature, for example in WO 2005/014689. This and the literature cited therein is incorporated into the present application by way of reference.

Monomers which lead to structural units of the formula (1) in polymers and dendrimers according to the invention are preferably selected from formula (1)

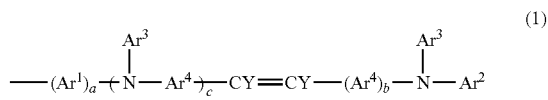

in which $Ar^{1-4}$, a, b and c have the meanings indicated above and in which one of the substituents $R^1$ on $Ar^1$ and optionally one of the substituents $R^2$ on $Ar^2$ and one of the substituents $R^3$ on $Ar^3$ each, independently of one another, denote a reactive group Z which is suitable for a polymerisation reaction.

The present invention likewise relates to novel monomers which lead to units of the formula (1) in the polymer and dendrimer, in particular novel monomers of the formula (1) and preferred sub-formulae thereof.

Particularly preferred groups Z are selected from halogen, in particular Cl, Br, I, O-tosylate, O-triflate, O—SO$_2$R', B(OH)$_2$, B(OR')$_2$ or Sn(R')$_3$, further-more O-mesylate, O-nonaflate, SiMe$_2$F, SiMeF$_2$, CR'=C(R')$_2$ or C≡CH, in which R' denotes optionally substituted alkyl or aryl, and two groups R' may form an aromatic or aliphatic, mono- or polycyclic ring system. "Aryl" and "alkyl" preferably have one of the meanings indicated above.

Preference is furthermore given to monomers of the sub-formulae (1a)-(1m) shown above in which the radicals V each, independently of one another, denote Z.

The monomers can be prepared by processes which are known to the person skilled in the art and are described in standard works of organic chemistry. Particularly suitable and preferred processes are described in the examples.

The polymers according to the invention have the following advantages over the polymers in accordance with the prior art:

(1) The polymers according to the invention exhibit higher photostability compared with polymers in accordance with the prior art. This is of crucial importance for use of these polymers since they must not be decomposed either by the radiation liberated by electroluminescence or by externally incident radiation. This property is still unsatisfactory in the case of polymers in accordance with the prior art.

(2) The polymers according to the invention have (with an otherwise identical or similar composition) comparable or higher luminous efficiencies in the application. This is of enormous importance since thus either the same brightness can be achieved with lower energy consumption, which is very important, in particular, in mobile applications (displays for mobile phones, pagers, PDAs, etc.) which rely on batteries. Conversely, higher brightnesses are obtained with the same energy consumption, which may be interesting, for example, for illumination applications.

(3) Furthermore, it has surprisingly been found that, again in direct comparison, the polymers according to the invention have comparable or longer operating lifetimes.

It may additionally be preferred to use the polymer according to the invention not as the pure substance, but instead as a mixture (blend) together with further polymeric, oligomeric, dendritic or low-molecular-weight sub-stances of any desired type. These may, for example, improve the electronic properties or emit themselves. The present invention therefore also relates to blends of this type.

The invention furthermore relates to solutions and formulations comprising one or more polymers or blends according to the invention in one or more solvents. The way in which polymer solutions can be prepared is known to the person skilled in the art and is described, for example, in WO 02/072714, WO 03/019694 and the literature cited therein.

These solutions can be used in order to produce thin polymer layers, for example by area-coating methods (for example spin coating) or by printing processes (for example ink-jet printing).

The solutions, formulations, blends or mixtures according to the invention may optionally also comprise further components or additives, for example one or more additives selected from the group consisting of surface-active substances, lubricants, wetting aids, dispersion aids, adhesion promoters, hydrophobicising agents, flow improvers, antifoams, deaerators, diluents, reactive diluents, auxiliaries for improving the scratch resistance, catalysts, sensitisers, stabilisers, for example against light, heat and oxidation, inhibitors, chaintransfer reagents, comonomers, dyes, pigments and nanoparticles.

The polymers according to the invention can be used in PLEDs. The way in which PLEDs can be produced is known to the person skilled in the art and is described in detail, for example, as a general process in WO 2004/070772, which should be adapted correspondingly for the individual case.

As described above, the polymers according to the invention are very particularly suitable as electroluminescent materials in PLEDs or displays produced in this way.

For the purposes of the invention, electroluminescent materials are taken to mean materials which can be used as active layer in a PLED. Active layer means that the layer is capable of emitting light on application of an electric field (light-emitting layer) and/or that it improves the injection and/or transport of the positive and/or negative charges (charge-injection or charge-transport layer).

The invention therefore also relates to the use of a polymer or blend according to the invention in a PLED, in particular as electroluminescent material.

The invention thus likewise relates to a PLED having one or more active layers, where at least one of these active layers comprises one or more polymers according to the invention. The active layer can be, for example, a light-emitting layer and/or a transport layer and/or a charge-injection layer.

The present application text and also the examples below are directed to the use of polymers or blends according to the invention in relation to PLEDs and corresponding displays. In spite of this restriction of the description, it is possible for the person skilled in the art, without further inventive step, also to use the polymers according to the invention as semiconductors for further uses in other electronic devices, for example in organic field-effect transistors (O-FETs), in organic integrated circuits (O-ICs), in organic thin-film transistors (O-TFTs), in organic solar cells (O-SCs), in organic laser diodes (O-lasers), or in organic photovoltaic (OPV) elements or devices, to mention but a few applications.

The present invention likewise relates to the use of polymers according to the invention in the corresponding devices.

It is likewise easy for the person skilled in the art to apply the descriptions given above for conjugated polymers to conjugated dendrimers without further inventive step. The present invention thus also relates to conjugated dendrimers of this type.

The following examples are intended to explain the invention without restricting it. In particular, the features, properties and advantages described therein of the defined compounds on which the particular example is based can also be applied to other compounds which are not indicated in detail, but fall within the scope of protection of the claims, unless stated otherwise elsewhere.

EXAMPLE 1

Synthesis of (4-bromophenyl)-{4-[(E)-2-(4-bromophenyl)-vinyl]phenyl}-(4-tert-butylphenyl)amine (Monomer M1 According to the Invention)

a) Synthesis of (4-tert-butylphenyl)phenylamine

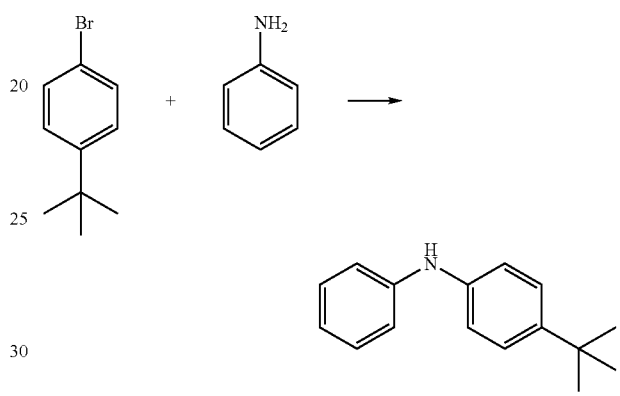

96.4 g (452 mmol) of 1-bromo-4-tert-butylbenzene and 42.1 g (452 mmol) of aniline are dissolved in toluene and saturated with $N_2$ for 15 min. 2.85 g (5 mmol) of DPPF, followed by 1.13 g (5 mmol) of Pd(OAc)$_2$ and 56.8 g (588 mmol) of NaO$^t$Bu are subsequently added successively, and the mixture is refluxed for 6 h. The organic phase is separated off, washed twice with water and filtered through Celite, rinsed with toluene and evaporated in a rotary evaporator, leaving 101 g of ochre-coloured solid (99% of theory), which is employed without further purification in the subsequent reaction.

b) Synthesis of 2-(4-bromophenyl)-1,3-dioxolane

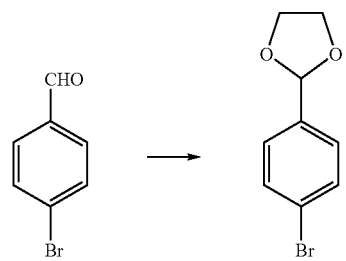

100 g (540 mmol) of 4-bromobenzaldehyde together with 200 mg of ptoluenesulfonic acid and 30 ml (540 mmol) of anhydrous ethylene glycol are initially introduced in 600 ml of toluene, and the mixture is refluxed on a water separator with monitoring by TLC. When the reaction is complete, the reaction solution is washed twice with sat. NaHCO$_3$ solution and once with water, dried over Na$_2$SO$_4$ and evaporated in a rotary evaporator, giving 123 g (99% of theory) of the dioxolane as a yellow oil.

c) Synthesis of (4-tert-butylphenyl)-(4-1,3-dioxolan-2-ylphenyl)phenylamine

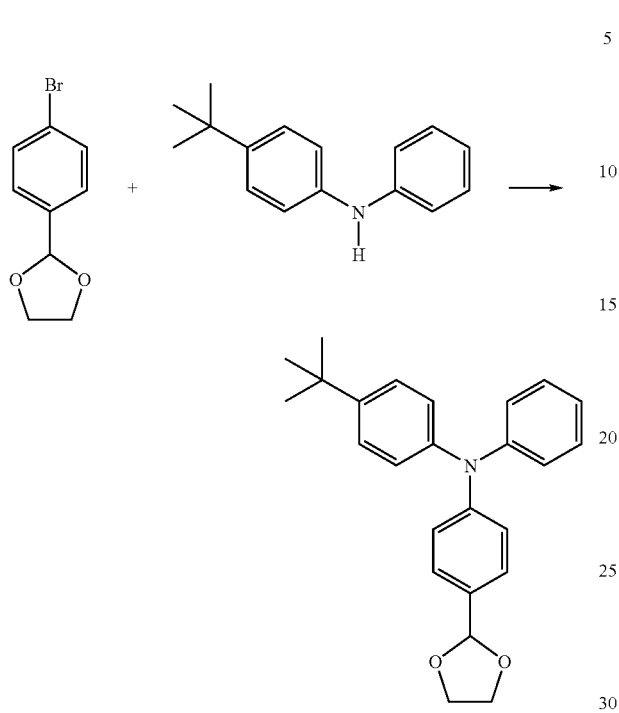

48.8 g (213 mmol) of 2-(4-bromophenyl)-1,3-dioxolane and 48 g (213 mmol) of (4-tert-butylphenyl)phenylamine are initially introduced in 750 ml of toluene, and the solution is saturated with N₂ for about 30 min. 29.2 g (304 mmol) of sodium tert-butoxide are subsequently added in small portions, followed by 760 mg (4.2 mmol) of chlorobis-t-butylphosphine and 485 mg (2.1 mmol) of Pd(OAc)₂. The mixture is refluxed for 3 h with monitoring by TLC.

When the reaction is complete, the reaction mixture is washed twice with water, and the organic phase is filtered through Celite and evaporated in a rotary evaporator, giving 79.4 g (99% of theory) of the product in the form of a yellow oil.

d) Synthesis of (4-tert-butylphenyl)-(4-formylphenyl)-4-bromophenyl amine

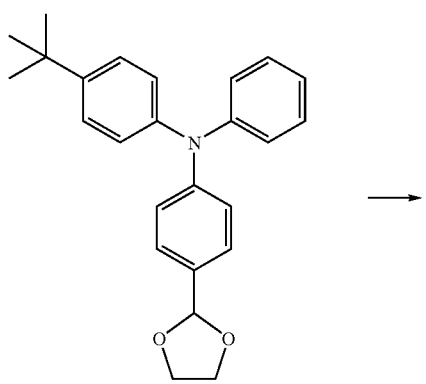

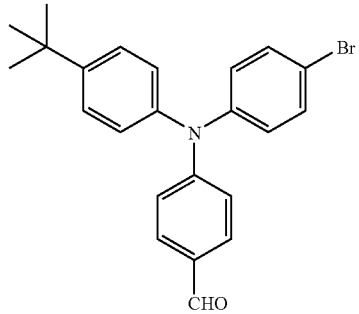

79.9 g (214.0 mmol) of the dioxolanyltriphenylamine are dissolved in 800 ml of THF under N₂, and 38.1 g (214.0 mmol) of NBS are added in small portions at RT over the course of 1 h, and the mixture is stirred for 1 h. The batch is evaporated in a rotary evaporator, and the residue is partitioned between ethyl acetate and water, washed twice with water, dried over Na₂SO₄ and evaporated in a rotary evaporator. The oily residue which remains is heated at the boil for 2 h in 400 ml of 80% acetic acid. The solid which precipitates after cooling is filtered off with suction and washed with water and methanol and dried, giving 87 g (88% of theory) of the product.

Synthesis of diethyl 4-bromobenzylphosphonate

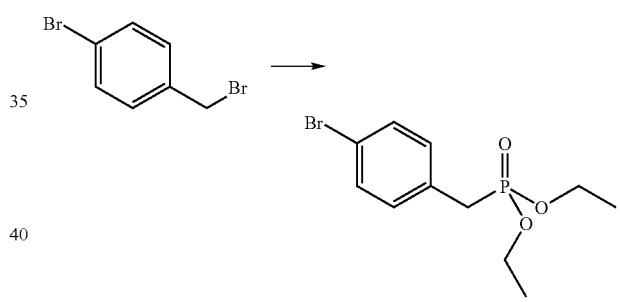

203.6 g (815 mmol) of 4-bromobenzyl bromide and 215 ml (1.2 mol) of triethyl phosphite are mixed and heated at 130° C. for 1 h with gas discharge. The product is then subjected to fractional distillation (2×10⁻² mbar, 120° C.), giving 224 g (89%) of the product as a colourless liquid.

Synthesis of (4-bromophenyl)-{4-[2-(4-bromophenyl)vinyl]phenyl}-(4-tert-butylphenyl)amine M1

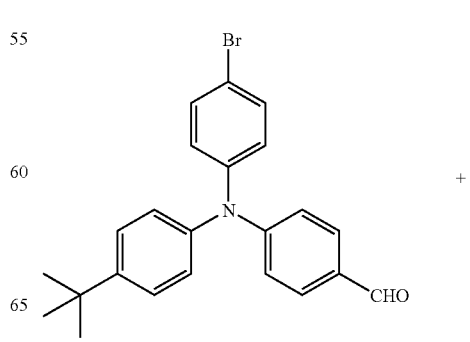

-continued

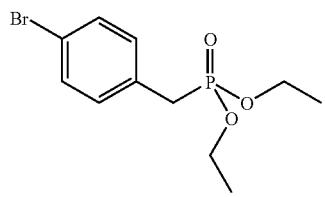

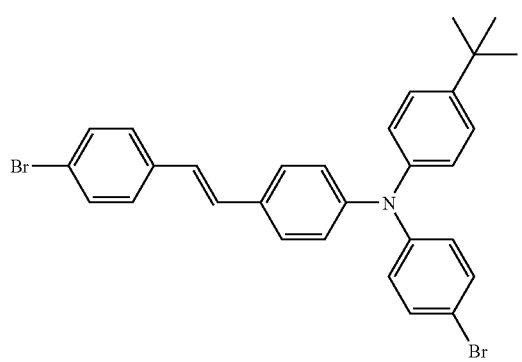

41 g (132 mmol) of the phosphonate are dissolved in 400 ml of dry DMF, 28 g (265 mmol) of NaO$^t$Bu are added at about 5° C., and, after 30 min, 49 g (120 mmol) of the triphenylamine aldehyde, dissolved in 200 ml of dried DMF, are added dropwise. After 2 h, 500 ml of ethanol and 500 ml of 4M HCl are added dropwise, and the precipitate is filtered off with suction, washed with water and EtOH and dried. The product is purified to a purity of >99.9% by recrystallisation six times from heptane, leaving 43 g (64%) of yellow, felt-like crystals.

EXAMPLE 2

Synthesis of Further Comonomers

The synthesis of monomers M2 to M5 is described in WO 03/020790 and the literature cited therein.

Monomer M2

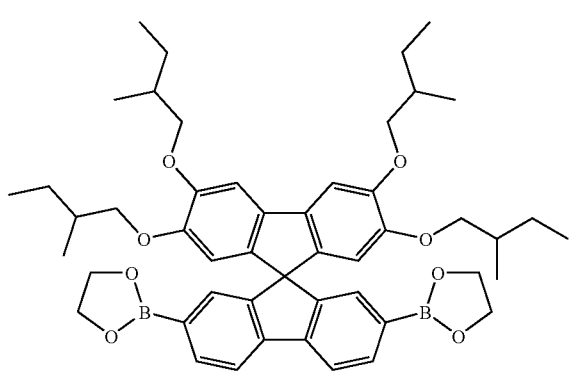

Monomer M3

Monomer M4

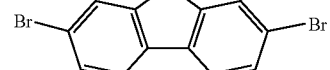

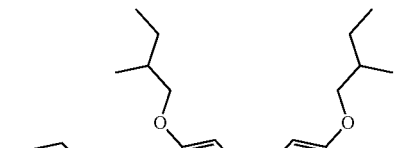

Monomer M5

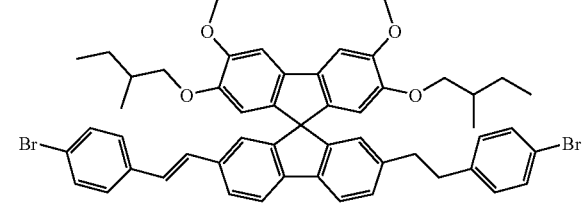

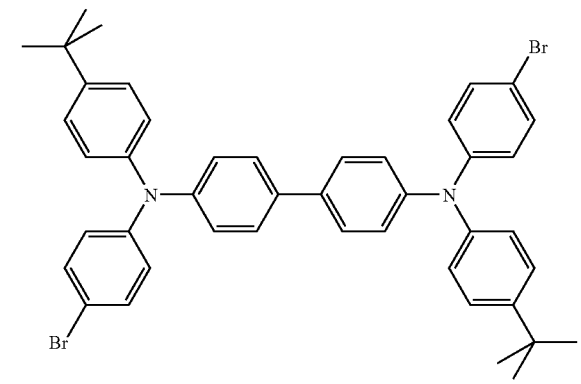

EXAMPLE 3

Synthesis of the Polymers

The polymers are synthesised by SUZUKI coupling as described in WO 03/048225. The composition of synthesised polymers P1 and P2 is shown in Table 1. In addition, comparative polymers C1 and C2 which contain monomer M4 instead of monomer M1, which results in units of the formula (1) in the polymer, are synthesised. The composition of these comparative polymers is likewise shown in Table 1

EXAMPLE 4

Production of PLEDs

The polymers are investigated for use in PLEDs. The PLEDs are in each case two-layer systems, i.e. substrate// ITO//PEDOT//polymer//cathode. PEDOT is a polythiophene derivative (Baytron P, from H. C. Starck, Goslar). The cathode used in all cases is Ba/Ag (Aldrich). The way in which PLEDs can be produced is described in detail in WO 04/037887 and the literature cited therein.

EXAMPLE 5

Device Examples

The results obtained on use of polymers P1 and P2 in PLEDs are shown in Table 1. Also shown are the electroluminescence results obtained using comparative polymers C1 and C2.

As can be seen from the results, the efficiency of the polymers according to the invention is better than that of the comparative polymers. The emission colour is comparable, and the lifetimes are significantly improved taking this into account. This shows that the polymers according to the invention are more suitable for use in displays than are polymers in accordance with the prior art.

TABLE 1

Device results

| Example | Polymer | Monomer | Max. eff./ cd/A | U@100 cd/m²/V | CIE x/y[a] | Lifetime[b]/ h |
|---|---|---|---|---|---|---|
| 5 | P1 | 10% M1 50% M2 30% M3 10% M5 | 5.02 | 3.7 | 0.16/0.27 | 250 |
| 6 | P2 | 2% M1 50% M2 46% M3 2% M5 | 6.35 | 4.1 | 0.15/0.18 | 1600 |
| 7 | C1[c] | 50% M2 30% M3 10% M5 10% M4 | 4.66 | 3.9 | 0.17/0.30 | 180 |
| 8 | C2[c] | 50% M2 46% M3 2% M5 2% M4 | 4.70 | 4.7 | 0.17/0.26 | 449 |

[a]CIE coordinates: colour coordinates from the Commission Internationale de l'Eclairage 1931
[b]Lifetime: time until the brightness drops to 50% of the initial brightness, initial brightness 400 cd/m²
[c]Comparative polymers

The invention claimed is:

1. A conjugated polymer or dendrimer comprising one or more units of formula (1)

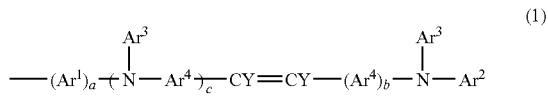

(1)

wherein
Ar¹ is, identically or differently on each occurrence, mono- or polycyclic aryl or heteroaryl optionally mono- or polysubstituted by $R^1$;
Ar² is, identically or differently on each occurrence, mono- or polycyclic aryl or heteroaryl optionally mono- or polysubstituted by $R^2$;
Ar³ is, identically or differently on each occurrence, mono- or polycyclic aryl or heteroaryl optionally mono- or polysubstituted by $R^3$;
Ar⁴ is, identically or differently on each occurrence, mono- or polycyclic aryl or heteroaryl optionally mono- or polysubstituted by $R^4$;
Y is, identically or differently on each occurrence, H, F, Cl, or a carbon or hydrocarbon radical having up to 40 C atoms, wherein two radicals Y, or one radical Y and an adjacent radical $R^1$, $R^4$, $Ar^1$, or $Ar^4$, optionally define an aliphatic or aromatic, mono- or polycyclic ring system;
$R^1$, $R^2$, $R^3$, and $R^4$
are, identically or differently on each occurrence, H, F, Cl, OH, CN, $N(R)_2$, $Si(R)_3$, $B(R)_2$, or a carbon or hydrocarbon radical having up to 40 C atoms, wherein two or more of the radicals $R^1$, $R^2$, $R^3$, and $R^4$ optionally define an aliphatic or aromatic, mono- or polycyclic ring system, and wherein $R^1$, $R^2$, and $R^3$ are optionally a covalent link in said polymer or dendrimer;
R is, identically or differently on each occurrence, H or a straight-chain, branched or cyclic alkyl having up to 22 C atoms, wherein one or more non-adjacent $CH_2$ groups are optionally replaced by —C(R⁰)=C(R⁰)—, —C≡C—, —N(R⁰)—, —Si(R⁰)₂—, —O—, —S—, —CO—, —CO—O—, —O—CO—, —O—CO—O—, —S—CO—, —CO—S—, with the proviso that O and/or S atoms are not linked directly to one another, and wherein one or more H atoms are optionally replaced by F, Cl, CN, or aryl having 5 to 40 C atoms, wherein one or more C atoms may be replaced by O, S or N, where these groups are optionally substituted by one or more non-aromatic radicals $R^1$; and wherein a plurality of radicals R, or radicals R with further radicals $R^1$, $R^2$, $R^3$, and $R^4$ optionally define an aromatic or aliphatic, mono- or polycyclic ring system;
R⁰ is, identically or differently on each occurrence, H or an aliphatic or aromatic hydrocarbon radical having up to 20 C atoms;
a is, identically or differently on each occurrence, 1, 2, or 3;
b is, identically or differently on each occurrence, 1, 2, or 3;
c is, identically or differently on each occurrence, 0 or 1.

2. The conjugated polymer or dendrimer of claim 1, wherein said units of formula (1) are in conjugation with the polymer main chain.

3. The conjugated polymer or dendrimer of claim 1, wherein said units of formula (1) are incorporated into the main chain of the polymer.

4. The conjugated polymer or dendrimer of claim 1, wherein said units of formula (1) are incorporated into the side chain of the polymer.

5. The conjugated polymer or dendrimer of claim 1, wherein the radicals R1, R2, R3, and R4 are selected from the group consisting of H, F, Cl, N(R)2, Si(R)3, B(R)2, straight-chain, branched, or cyclic alkyl having up to 22 C atoms optionally mono- or polysubstituted by F, Cl, Br, I, or CN, and wherein one or more non-adjacent CH2 groups are optionally replaced, independently of one another, by —C(R0)=C(R0)-, —N(R0)-, —Si(R0)2-, —O—, —S—, —CO—, —CO—O—, —O—CO—, —S—CO—, —CO—S—, —O—CO—O—, with the proviso that O and/or S atoms are not linked directly to one another, aryl having 5 to 40 C atoms, optionally mono- or polysubstituted by R wherein one or more C atoms are optionally replaced by O, S, or N, wherein R1, R2, and R3 are optionally a link in the polymer or dendrimer.

6. The conjugated polymer or dendrimer of claim 1, wherein Ar1, Ar2, and Ar3 are phenyl or phenylene optionally mono- or polysubstituted by R5, and Ar4 is selected from the group consisting of phenylene; 4,4'-biphenylene; 9,9-disubstituted fluorene-2,7-diyl; 6,6,12,12-tetrasubstituted indenofluorene-2,8-diyl, and spirobifluorene-2,7-diyl, each of which is optionally mono- or polysubstituted by R5, which is, identically or differently on each occurrence, H, F, Cl, OH, CN, N(R)2, Si(R)3, B(R)2, or a carbon or hydrocarbon radical having up to 40 C atoms.
7. The conjugated polymer or dendrimer of claim 1, wherein said units of formula (1) are selected from the group consisting the following sub-formulae:
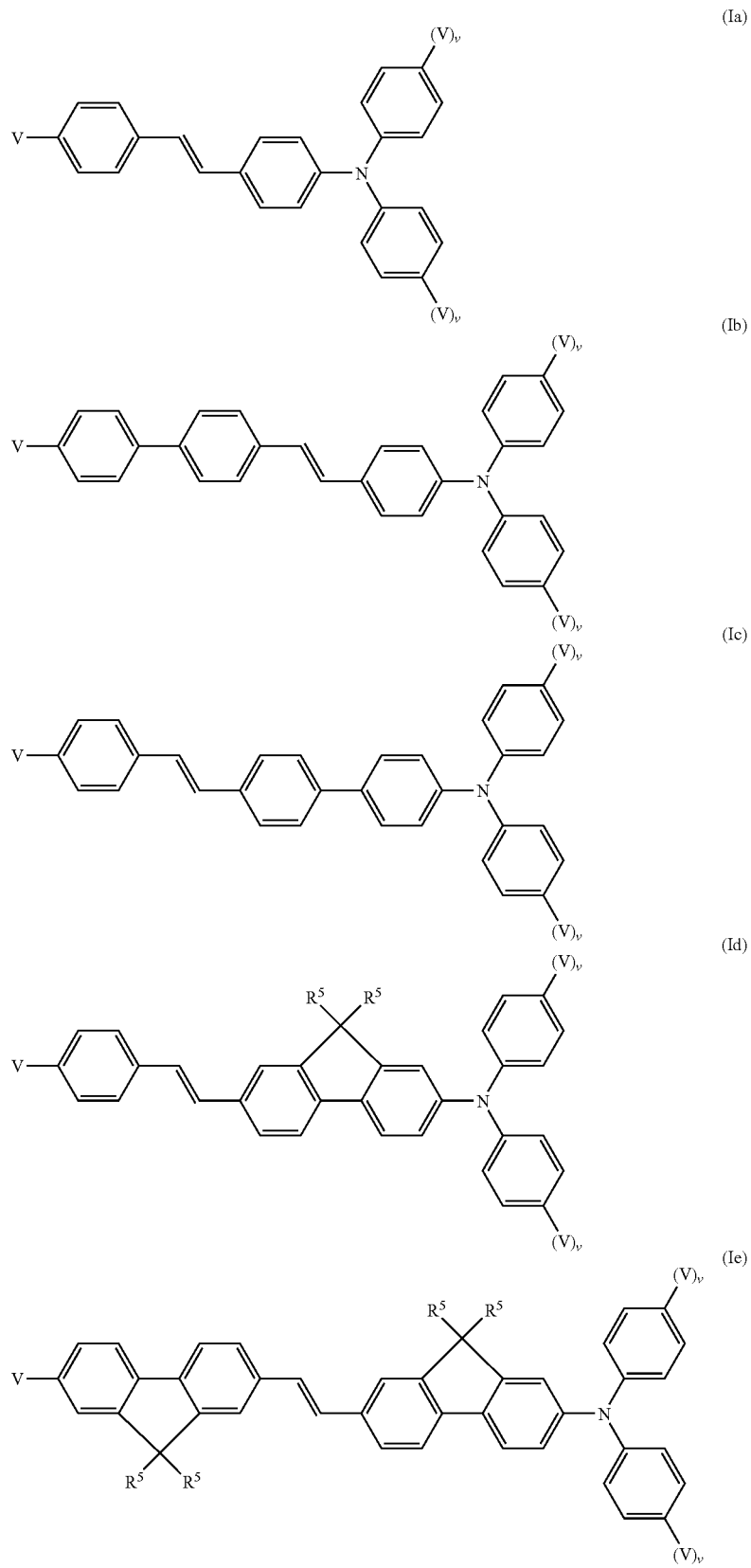

-continued
(1f)
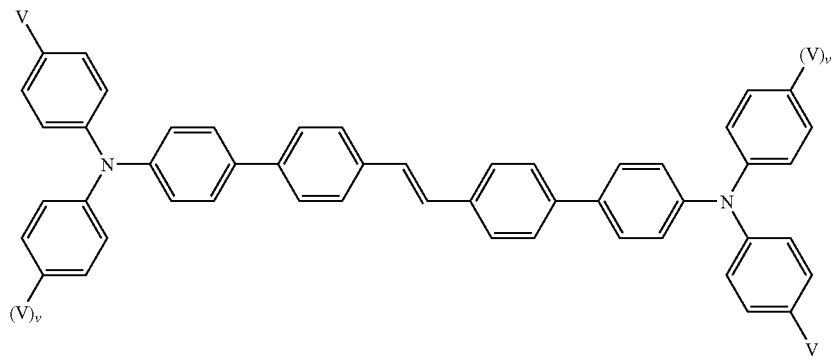
(1g)
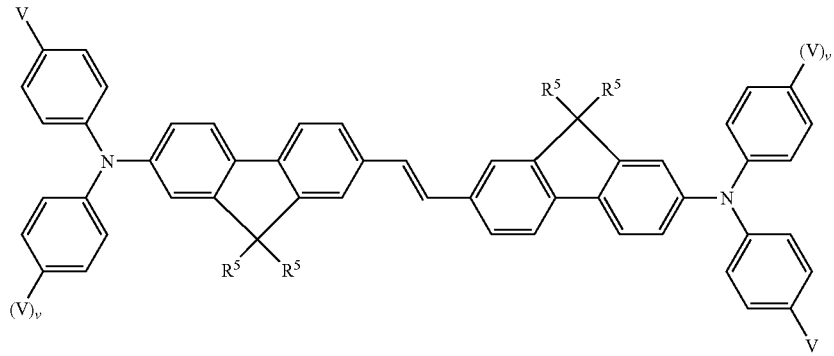
(1h)
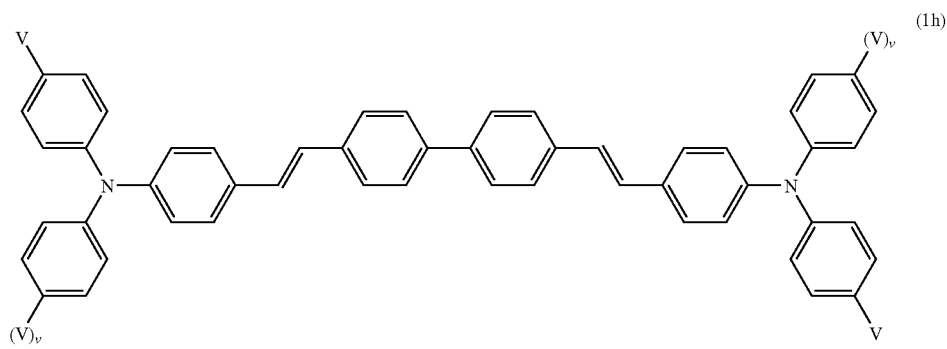
(1i)
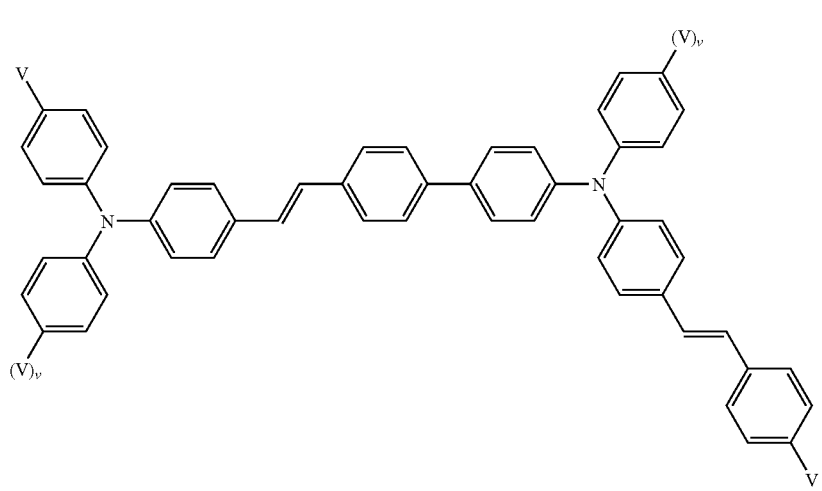

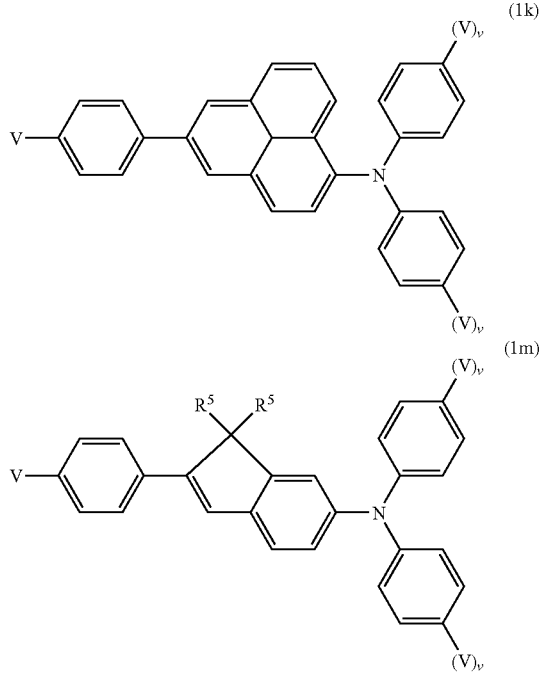

(1k)

(1m)

wherein V is a covalent link in said polymer or dendrimer, and v is 0 or 1, R5 is, identically or differently on each occurrence, H, F, Cl, OH, CN, N(R)2, Si(R)3, B(R)2, or a carbon or hydrocarbon radical having up to 40 C atoms, and the phenyl rings are optionally mono- or polysubstituted by R5.

8. The conjugated polymer or dendrimer of claim 1, further comprising structural elements selected from the group consisting of fluorenylenes, spirobifluorenylenes, dihydrophenanthrenylenes, tetrahydropyrenylenes, stilbenzylenes, bisstyrylarylenes, 1,4-phenylenes, 1,4-naphthylenes, 1,4-anthrylenes, 9,10-anthrylenes, 1,6-pyrenylenes, 2,7-pyrenylenes, 4,9-pyrenylenes, 3,9-perylenylenes, 3,10-perylenylenes, 2,7-phenanthrenylenes, 3,6-phenanthrenylenes, 4,4'-biphenylylenes, 4,4"-terphenylylenes, and 4,4'-bi-1,1'-naphthylylenes.

9. The conjugated polymer or dendrimer of claim 1, further comprising structural elements selected from the group consisting of triarylamines, triarylphosphines, benzidines, tetraarylene-para-phenylenediamines, phenothiazines, phenoxazines, dihydrophenazines, thianthrenes, dibenzo-p-dioxins, phenoxathiynes, carbazoles, azulenes, thiophenes, pyrroles, and furans.

10. The conjugated polymer or dendrimer of claim 1, further comprising structural elements selected from the group consisting of pyridines, pyrimidines, pyridazines, pyrazines, anthracenes, triarylboranes, oxadiazoles, quinolines, quinoxalines, and phenazines.

11. The conjugated polymer or dendrimer of claim 8, further comprising at least 50 mol % of structural elements selected from the group consisting of fluorenylenes, spirobifluorenylenes, dihydrophenanthrenylenes, tetrahydropyrenylenes, stilbenzylenes, bisstyrylarylenes, 1,4-phenylenes, 1,4-naphthylenes, 1,4-anthrylenes, 9,10-anthrylenes, 1,6-pyrenylenes, 2,7-pyrenylenes, 4,9-pyrenylenes, 3,9-perylenylenes, 3,10-perylenylenes, 2,7-phenanthrenylenes, 3,6-phenanthrenylenes, 4,4'-biphenylylenes, 4,4"-terphenylylenes, and 4,4'-bi-1,1'-naphthylylenes and from 2 to 30 mol % of structural elements selected from the group consisting of triarylamines, triarylphosphines, benzidines, tetraarylene-para-phenylenediamines, phenothiazines, phenoxazines, dihydro-phenazines, thianthrenes, dibenzo-p-dioxins, phenoxathiynes, carbazoles, azulenes, thiophenes, pyrroles, and furans.

12. The conjugated polymer or dendrimer of claim 1, wherein the proportion of structural units of formula (1) is from 1 to 10 mol %.

13. The conjugated polymer or dendrimer of claim 1, wherein the proportion of structural units of formula (1) is from 0.01 to 1 mol % and said polymer is white-emitting.

14. The conjugated polymer or dendrimer of claim 1, wherein said conjugated polymer or dendrimer comprises at least 1 mol % of structural units of the formula (1) and said polymer is red-emitting.

15. A blend of one or more polymers or dendrimers of claim 1 with one or more further polymeric, oligomeric, dendritic, or low-molecular-weight substances.

16. A monomeric compound of formula (1)

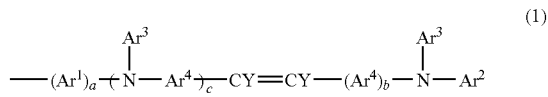

wherein
Ar$^1$ is, identically or differently on each occurrence, mono- or polycyclic aryl or heteroaryl optionally mono- or polysubstituted by R$^1$;
Ar$^2$ is, identically or differently on each occurrence, mono- or polycyclic aryl or heteroaryl optionally mono- or polysubstituted by R$^2$;

Ar³ is, identically or differently on each occurrence, mono- or polycyclic aryl or heteroaryl optionally mono- or polysubstituted by R³;

Ar⁴ is, identically or differently on each occurrence, mono- or polycyclic aryl or heteroaryl optionally mono- or polysubstituted by R⁴;

a is, identically or differently on each occurrence, 1, 2, or 3;
b is, identically or differently on each occurrence, 1, 2, or 3;
c is, identically or differently on each occurrence, 0 or 1; and wherein one of the substituents R¹ on Ar¹ and optionally one of the substituents R² on Ar² and/or one of the substituents R³ on Ar³ are each, independently of one another, a reactive group Z suitable for a polymerisation reaction.

17. The monomer of claim 16, wherein $Z^1$ and $Z^2$ are each, independently of one another, Cl, Br, I, O-tosylate, O-triflate, O—SO$_2$R', B(OH)$_2$, B(OR')$_2$, or Sn(R')$_3$, wherein R' is optionally substituted alkyl or aryl, and wherein two groups R' optionally define an aromatic or aliphatic, mono- or polycyclic ring system.

18. The monomer of claim 16, wherein they are selected from the sub-formulae (1a)-(1m)

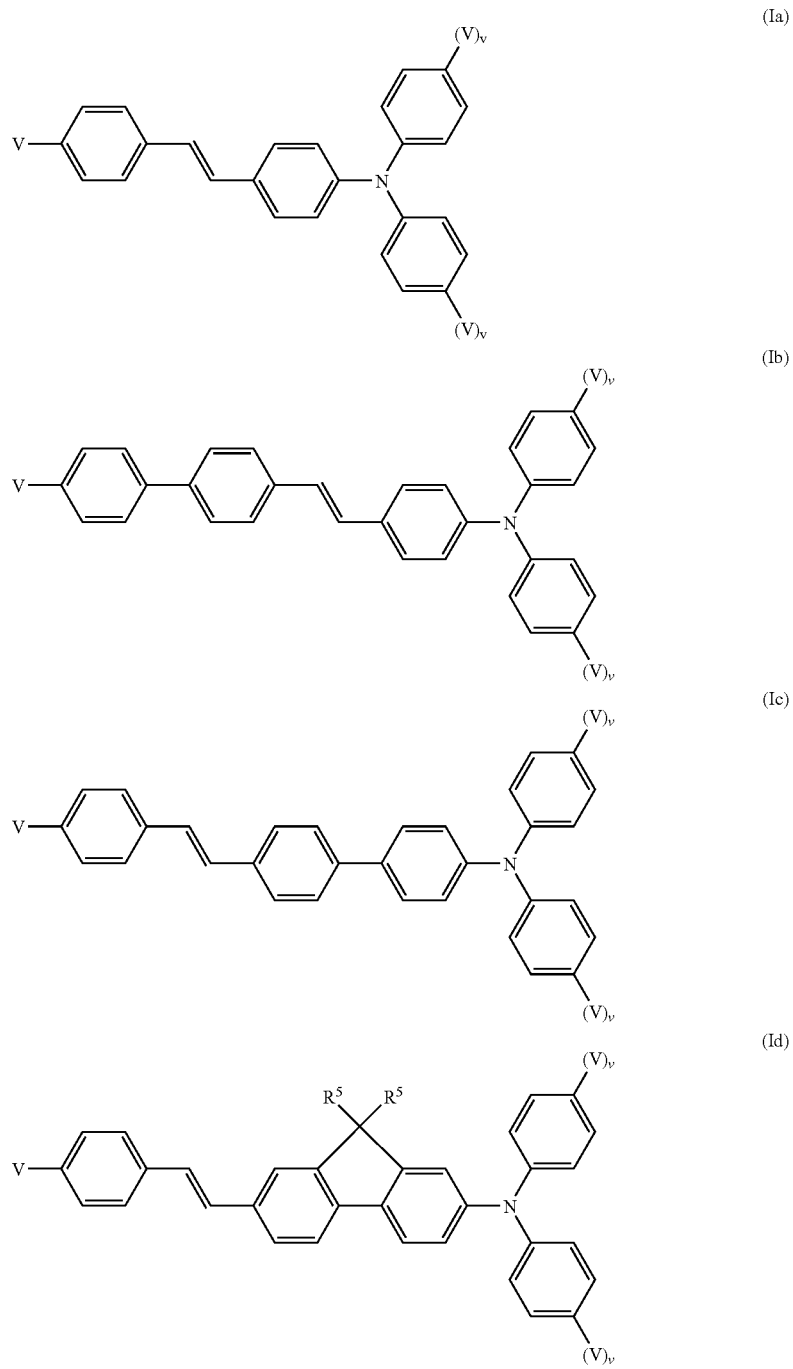

-continued
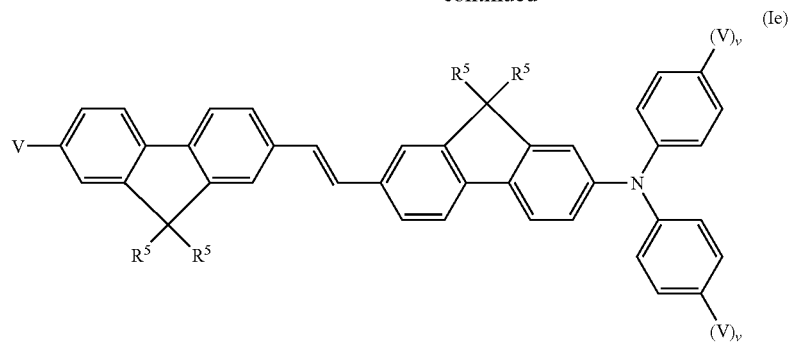
(Ie)
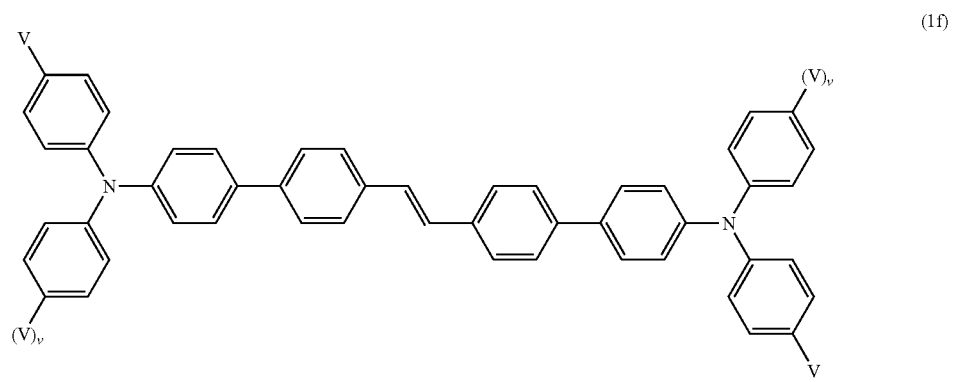
(1f)
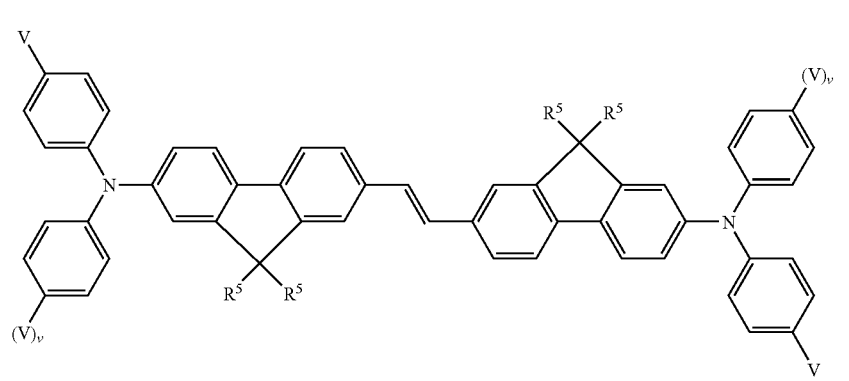
(1g)
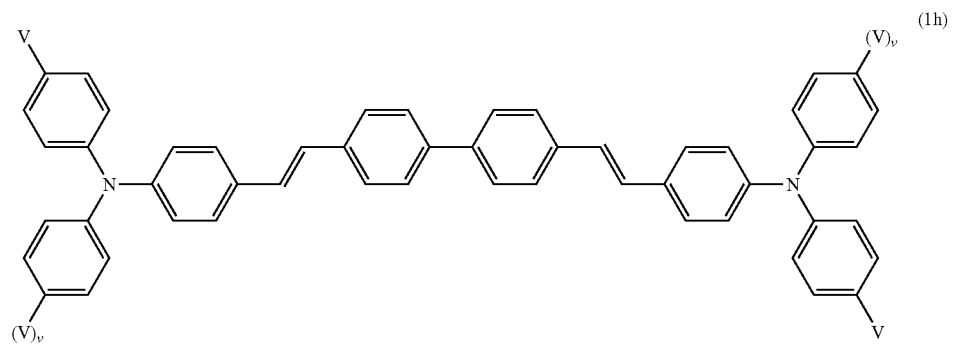
(1h)

(1i)

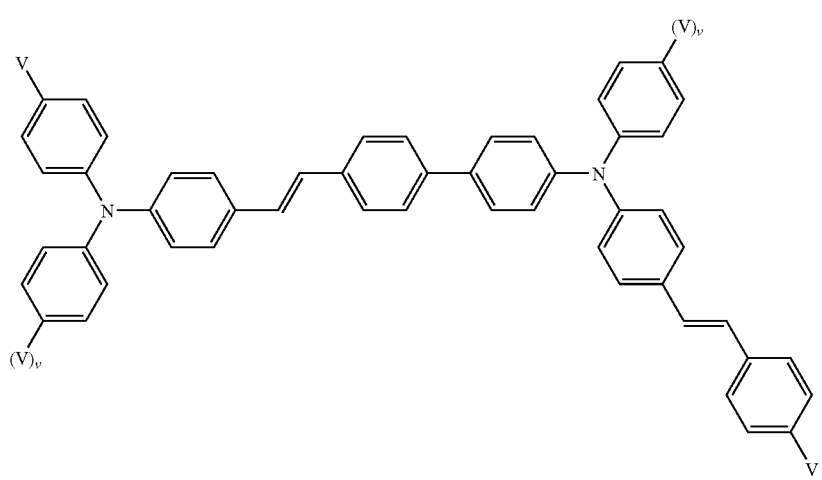

(1k)

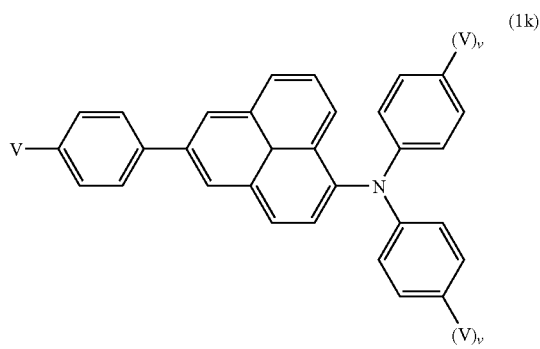

(1m)

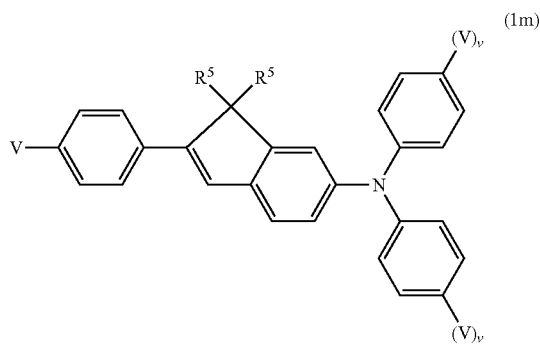

wherein radicals V are each, independently of one another, reactive groups suitable for a polymerisation reaction.

19. A solution or formulation comprising one or more polymers or dendrimers of claim 1 in one or more solvents.

20. An electronic component comprising one or more polymers or dendrimers of claim 1.

21. The electronic component of claim 20, wherein said electronic component is selected from the group consisting of organic field-effect transistors, organic thin-film transistors, organic integrated circuits, organic solar cells, organic light-emitting diodes, organic laser diodes, organic photovoltaic elements, and organic photovoltaic devices.

22. The organic light-emitting diode of claim 21, wherein said organic light-emitting diode comprises one or more layers comprising one or more conjugated polymers or dendrimers comprising one or more units of formula (1)

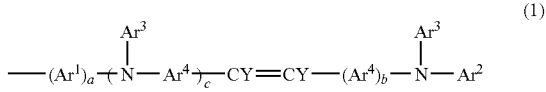

wherein

Ar$^1$ is, identically or differently on each occurrence, mono- or polycyclic aryl or heteroaryl optionally mono- or polysubstituted by R$^1$;

Ar² is, identically or differently on each occurrence, mono- or polycyclic aryl or heteroaryl optionally mono- or polysubstituted by R²;

Ar³ is, identically or differently on each occurrence, mono- or polycyclic aryl or heteroaryl optionally mono- or polysubstituted by R³;

Ar⁴ is, identically or differently on each occurrence, mono- or polycyclic aryl or heteroaryl optionally mono- or polysubstituted by R⁴;

Y is, identically or differently on each occurrence, H, F, Cl, or a carbon or hydrocarbon radical having up to 40 C atoms, wherein two radicals Y, or one radical Y and an adjacent radical R¹, R⁴, Ar¹, or Ar⁴, optionally define an aliphatic or aromatic, mono- or polycyclic ring system;

R¹, R², R³, and R⁴
are, identically or differently on each occurrence, H, F, Cl, OH, CN, Si(R)₃, B(R)₂, or a carbon or hydrocarbon radical having up to 40 C atoms, wherein two or more of the radicals R¹, R², R³, and R⁴ optionally define an aliphatic or aromatic, mono- or polycyclic ring system, and wherein R¹, R², and R³ are optionally a covalent link in said polymer or dendrimer;

R is, identically or differently on each occurrence, H or a straight-chain, branched or cyclic alkyl having up to 22 C atoms, wherein one or more non-adjacent CH, groups are optionally replaced by —C(R⁰)=C(R⁰)—, —C≡C—, —N(R⁰)—, —Si(R⁰)₂—, —O—, —S—, —CO—, —CO—O—, —O—CO—, —O—CO—O—, —S—CO—, —CO—S—, with the proviso that O and/or S atoms are not linked directly to one another, and wherein one or more H atoms are optionally replaced by F, Cl, CN, or aryl having 5 to 40 C atoms, wherein one or more C atoms may be replaced by O, S or N, where these groups are optionally substituted by one or more non-aromatic radicals R¹; and wherein a plurality of radicals R, or radicals R with further radicals R¹, R², R³, and R⁴ optionally define an aromatic or aliphatic, mono- or polycyclic ring system;

R⁰ is, identically or differently on each occurrence, H or an aliphatic or aromatic hydrocarbon radical having up to 20 C atoms;

a is, identically or differently on each occurrence, 1, 2, or 3;
b is, identically or differently on each occurrence, 1, 2, or 3;
c is, identically or differently on each occurrence, 0 or 1.

23. A process for preparing the compounds of claim 16 comprising reacting optionally substituted phenyl-4-bromophenyl-4-formylphenylamine with optionally substituted diethyl 4-bromobenzylphosphonate in the presence of a base.

* * * * *

UNITED STATES PATENT AND TRADEMARK OFFICE
CERTIFICATE OF CORRECTION

PATENT NO. : 7,799,875 B2
APPLICATION NO. : 12/097782
DATED : September 21, 2010
INVENTOR(S) : Arne Buesing et al.

Page 1 of 1

It is certified that error appears in the above-identified patent and that said Letters Patent is hereby corrected as shown below:

At column 15, formula (XXII), near line number 50, "R6" should read --$R^6$--; and At column 16, formula (XXV), near line number 8, "R5" should read --$R^5$--.

At column 30, claim number 5, line number 48, "R1, R2, R3 and R4" should read --$R^1$, $R^2$, $R^3$, and $R^4$--;

At column 30, claim number 5, line number 49, "N(R)2, Si(R)3, B(R)2" should read --$N(R)_2$, $Si(R)_3$, $B(R)_2$--;

At column 30, claim number 5, line number 52, "CH2" should read --$CH_2$--;

At column 30, claim number 5, line number 54, "—N(R0)-, —Si(R0)2-" should read -- —$N(R^0)$-, —$Si(R^0)_2$- --;

At column 30, claim number 5, line number 59, "R1, R2" should read --$R^1$, $R^2$--;

At column 30, claim number 5, line number 60, "R3" should read --$R^3$--;

At column 30, claim number 6, line 62, "Ar1, Ar2, Ar3" should read --$Ar^1$, $Ar^2$, $Ar^3$--;

At column 30, claim number 6, line 63, "R5 and Ar4" should read --$R^5$ and $Ar^4$--;

At column 30, claim number 6, line 67, "R5" should read --$R^5$--;

At column 31, claim number 6, line 2, "N(R)2, Si(R)3, B(R)2" should read --$N(R)_2$, $Si(R)_3$, $B(R)_2$--;

At column 35, claim number 7, line 32, "R5" should read --$R^5$--;

At column 35, claim number 7, line 33, "N(R)2, Si(R)3, B(R)2" should read -- $N(R)_2$, $Si(R)_3$, $B(R)_2$; and At column 35, claim number 7, line 36, "R5" should read --$R^5$--.

Signed and Sealed this
Eleventh Day of October, 2011

David J. Kappos
*Director of the United States Patent and Trademark Office*